United States Patent
Jung et al.

(10) Patent No.: US 6,368,768 B1
(45) Date of Patent: Apr. 9, 2002

(54) ORGANIC ANTI-REFLECTIVE COATING MATERIAL AND ITS PREPARATION

(75) Inventors: e;.5qMin-Ho Jung; Sung-Eun Hong; Ki-Ho Baik, all of Gyunggi-do (KR)

(73) Assignee: Hyundai Electronics Industries Co., Ltd. (KR)

( * ) Notice: Subject to any disclaimer, the term of this patent is extended or adjusted under 35 U.S.C. 154(b) by 0 days.

(21) Appl. No.: 09/501,049

(22) Filed: Feb. 9, 2000

(30) Foreign Application Priority Data

Apr. 23, 1999 (KR) .............................. 99-14763

(51) Int. Cl.$^7$ ........................... G03F 7/004; C08F 18/00
(52) U.S. Cl. ............................ 430/270.1; 430/271.1; 526/315; 526/320; 526/326; 526/329.7
(58) Field of Search ................. 430/270.1, 271.1; 526/326, 320, 315, 329.7

(56) References Cited

U.S. PATENT DOCUMENTS

| | | | |
|---|---|---|---|
| 4,315,089 A | * 2/1982 | Naarmann et al. | 526/89 |
| 4,822,718 A | 4/1989 | Latham et al. | 430/271 |
| 5,258,477 A | * 11/1993 | Tsai et al. | 526/315 |
| 5,674,648 A | 10/1997 | Brewer et al. | 430/18 |
| 5,886,102 A | * 3/1999 | Sinta et al. | 525/154 |

\* cited by examiner

*Primary Examiner*—Rosemary Ashton
(74) *Attorney, Agent, or Firm*—Townsend and Towsend and Crew LLP

(57) ABSTRACT

Polymers are provided having the following formula I, II or III:

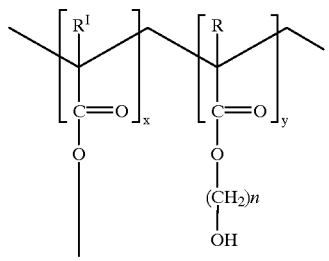

(general formula I)

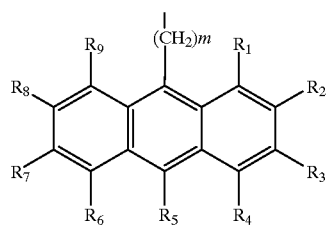

(general formula II)

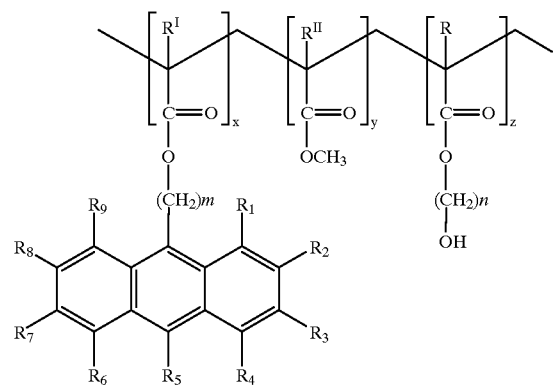

Polymers of the present invention can be used to provide an anti-reflective coating (ARC) material useful for submicrolithography processes using 248 nm KrF, 193 nm ArF and 157 nm $F_2$ lasers. The polymers contain chromophore substituents which exhibit sufficient absorbance at wavelengths useful for such submicrolithography process. The ARC prevents back reflection from the surface of or lower layers in the semiconductor devices and solves the problem of the CD being altered by the diffracted and reflected light from such lower layers. The ARC also eliminates the standing waves and reflective notching due to the optical properties of lower layers on the wafer, and due to the changes in the thickness of the photosensitive film applied thereon. This results in the formation of stable ultrafine patterns suitable for 64M, 256M, 1 G, 4 G and 16 G DRAM semiconductor devices and a great improvement in the production yield.

41 Claims, No Drawings

ORGANIC ANTI-REFLECTIVE COATING MATERIAL AND ITS PREPARATION

CROSS-REFERENCES TO RELATED APPLICATIONS

This application is related to Korean Patent Application No. 99-14763, filed Apr. 23, 1999, and takes priority from that date.

BACKGROUND OF THE INVENTION

1. Field of the Invention

The present invention relates to an organic anti-reflective coating material which allows the stable formation of ultrafine patterns suitable for 64M, 256M, 1 G, 4 G and 16 G DRAM semiconductor devices. More particularly, the present invention relates to an organic anti-reflective coating material which contains a chromophore with high absorbance at the wavelengths useful for submicrolithography. A layer of said anti-reflection material can prevent back reflection of light from lower layers or the surface of the semiconductor chip, as well as eliminate the standing waves in the photoresist layer, during a submicrolithographic process using a 248 nm KrF, 193 nm ArF or 157 nm $F_2$ laser light sources. Also, the present invention is concerned with an anti-reflective coating composition comprising such a material, an anti-reflective coating therefrom and a preparation method thereof.

2. Description of the Prior Art

During a submicrolithographic process, one of the most important processes for fabricating highly integrated semiconductor devices, there inevitably occur standing waves and reflective notching of the waves due to the optical properties of lower layers coated on the wafer and to changes in the thickness of the photosensitive film applied thereon. In addition, the submicrolithographic process generally suffers from a problem of the CD (critical dimension) being altered by diffracted and reflected light from the lower layers.

To overcome these problems, it has been proposed to introduce a film, called an anti-reflective coating (hereinafter sometimes referred to as "ARC"), between the substrate and the photosensitive film. Generally, ARCs are classified as "organic" and "inorganic" depending on the materials used, and as "absorptive" and "interfering" depending on the mechanism of operation. In microlithographic processes using I-line (365 nm wavelength) radiation, inorganic ARCs, for example TiN or amorphous carbon coatings, are employed when advantage is taken of an absorption mechanism, and SiON coatings are employed when an interference mechanism is employed. The SiON ARCs are also adapted for submicrolithographic processes which use KrF light sources.

Recently, extensive and intensive research has been and continues to be directed to the application of organic ARCs for such submicrolithography. In view of the present development status, organic ARCs must satisfy the following fundamental requirements to be useful:

First, the peeling of the photoresist layer due to dissolution in solvents in the organic ARC should not take place when conducting a lithographic process. In this regard, the organic ARC materials have to be designed so that their cured films have a crosslinked structure without producing by-products.

Second, there should be no migration of chemical materials, such as amines or acids, into and from the ARCs. If acids are migrated from the ARC, the photosensitive patterns are undercut while the egress of bases, such as amines, causes a footing phenomena.

Third, faster etch rates should be realized in the ARC than in the upper photosensitive film, allowing an etching process to be conducted smoothly with the photosensitive film serving as a mask.

Finally, the organic ARCs should be as thin as possible while playing an excellent role in preventing light reflection.

Despite the variety of ARC materials, those which are satisfactorily applicable to submicrolithographic processes using ArF light have not been found, thus far. As for inorganic ARCs, there have been reported no materials which can control the interference at the ArF wavelength, that is, 193 nm. As a result, active research has been undertaken to develop organic materials which act as superb ARCs. In fact, in most cases of submicrolithography, photosensitive layers are necessarily accompanied by organic ARCs which prevent the standing waves and reflective notching occurring upon light exposure, and eliminate the influence of the back diffraction and reflection of light from lower layers. Accordingly, the development of such an ARC material showing high absorption properties against specific wavelengths is one of the hottest and most urgent issues in the art.

U.S. Pat. No. 4,910,122 discloses an ARC which is interposed under photosensitive layers to eliminate defects caused by reflected light. The coating described therein can be formed thinly, smoothly and uniformly and includes a light absorbing dye which eliminates many of the defects caused by reflected light, resulting in increased sharpness of the images in photosensitive materials. These types of ARCs, however, suffer from disadvantages of being complicated in formulation, extremely limited in material selection and difficult to apply for photolithography using Deep Ultraviolet (DUV) radiation. For example, the ARC of the above reference comprises 4 dye compounds, including polyamic acid, curcumin, Bixin and Sudan Orange G, and 2 solvents, including cyclohexanone and N-methyl-2-pyrrolidone. This multi-component system is not easy to formulate and may intermix with the resist composition coated thereover, bringing about undesired results.

SUMMARY OF THE INVENTION

Therefore, it is an object of the present invention to overcome the problems encountered in the prior art and to provide a novel organic compound which can be used as an ARC for submicrolithography using 193 nm ArF, 248 nm KrF and 157 nm $F_2$ lasers.

It is another object of the present invention to provide a method for preparing an organic compound which prevents the diffusion and reflection caused by the light exposure in submicrolithography.

It is a further object of the present invention to provide an ARC composition containing such a diffusion/reflection-preventive compound and a preparation method therefor.

It is a still further object of the present invention to provide an ARC formed from such a composition and a preparation method therefor.

The present invention pertains to acrylate polymer resins which can be used as an ARC. Preferred polymer resins contain a chromophore which exhibits high absorbance at 193 nm and 248 nm wavelengths. A crosslinking mechanism between alcohol groups and other functional groups is introduced into the polymer resins, so that a crosslinking reaction takes place when coatings of the polymer resins are "hard baked", thereby greatly improving the formation, tightness and dissolution properties of the ARCs. In particular, optimum crosslinking reaction efficiency and storage stability are realized in the present invention. The ARC resins of the present invention show superior solubility in all hydrocarbon solvents, but are of so high solvent resistance after hard baking that they are not dissolved in any solvent at all. These advantages allow the resins to be coated without any problem, and the coating prevents the undercutting and footing problems which can occur upon forming images on photosensitive materials. Furthermore, the coatings made of the acrylate polymers of the present invention are higher in etch rate than photosensitive films, improving the etch selection ratio therebetween.

DETAILED DESCRIPTION OF THE INVENTION

The ARC resins of the present invention are selected from the group consisting of acrylate polymers represented by the following general formulas I, II and III:

(general formula I)

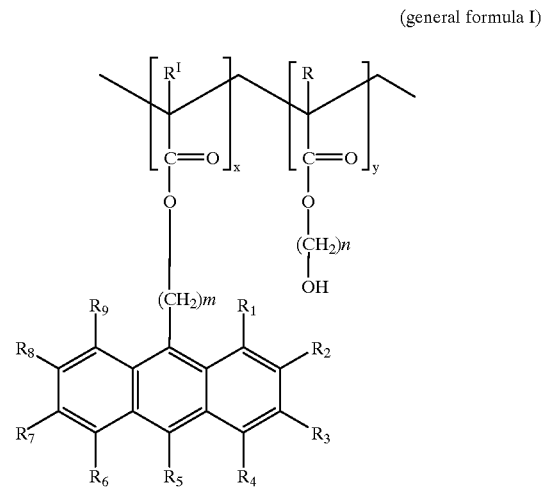

(general formula II)

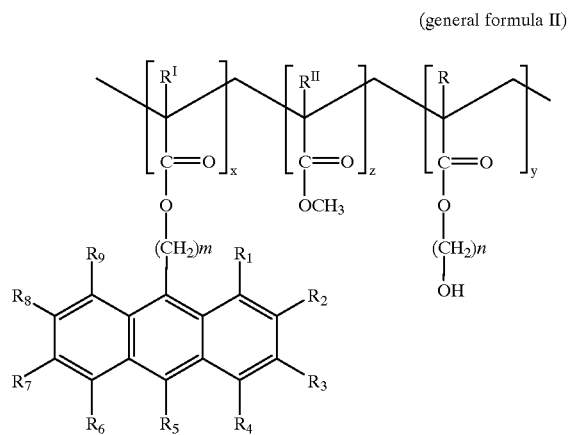

-continued (general formula III)

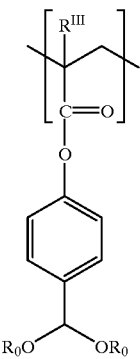

wherein, $R$, $R^I$, $R^{II}$, and $R^{III}$ are independently hydrogen or a methyl group;

$R_0$ is a methyl group or an ethyl group;

$R_1$ to $R_9$, which are the same or different, each represents hydrogen, hydroxy, methoxycarbonyl, carboxyl, hydroxymethyl, or a substituted or unsubstituted, linear or branched $C_1$–$C_6$ alkyl, alkane, alkoxyalkyl or alkoxyalkane;

x, y and z each is a mole fraction in the range from 0.01 to 0.99; and m and n are independently an integer of 1 to 4. In a preferred compound of Formula I, m is 1 or 2 and n is an integer of 1 to 4. In a preferred compound of Formula II, m is 1 or 2 and n is an integer from 2 to 4.

The polymers of the present invention are designed to provide greater absorbance at 193 nm and 248 nm wavelengths. To accomplish this result, a chromophore substituent which is able to absorb light at a wavelength of 193 nm as well as 248 nm is grafted to the backbone of the polymer.

The polymer of the general formula I, as illustrated in the following reaction formula 1, can be prepared by polymerizing 9-anthracenemethyl acrylate type monomers (I) and hydroxy alkylacrylate type monomers (II) with the aid of an initiator in a solvent. Each of the monomers has a mole fraction ranging from 0.01 to 0.99.

(reaction formula 1)

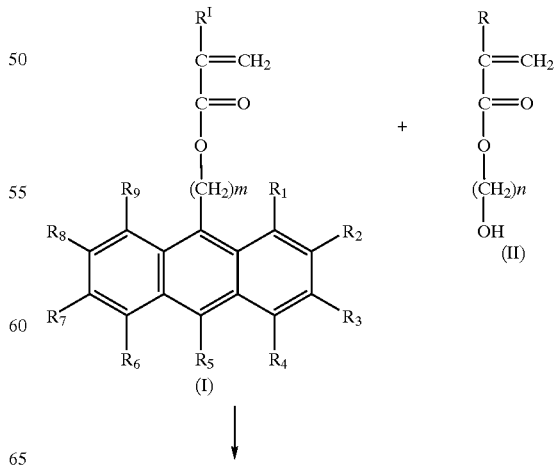

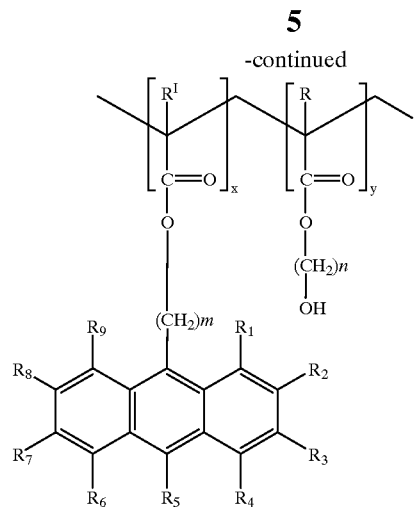

wherein R, $R^I$, $R_1$ to $R_9$, x, y, m and n each is as defined above.

The polymers of the general formula II can be prepared in a similar manner to the polymers of the general formula I, using 9-anthracenemethyl acrylate type monomers (I), hydroxy alkylacrylate type monomers (II) and methyl-methacrylate monomers (III) at a mole fraction of 0.01 to 0.99 for each monomer, as illustrated in the following reaction formula 2:

(reaction formula 2)

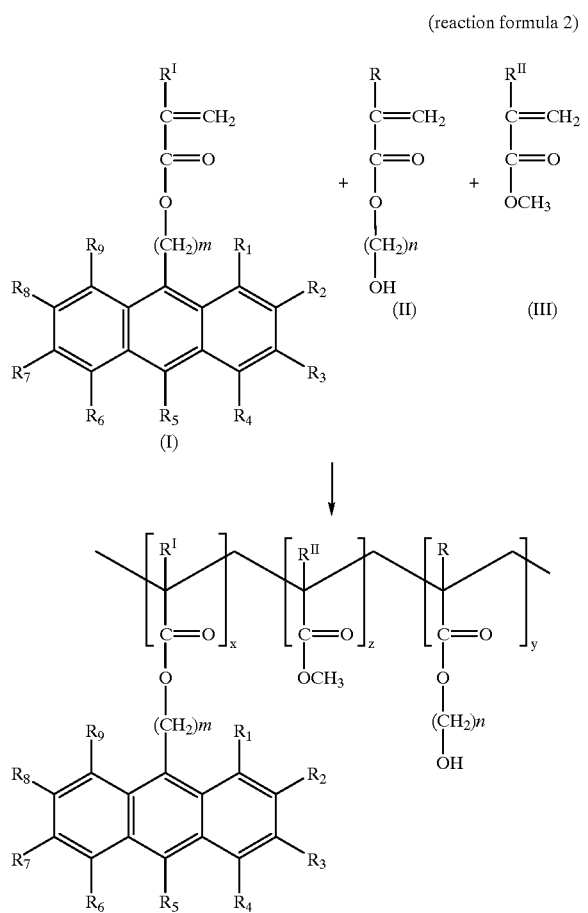

wherein R, $R^I$, $R^{II}$, $R_1$ to $R_9$, x, y, z, m and n each is as defined above.

The preparation of the polymer of the general formula III is illustrated in the following reaction formula 3. As shown, first, methacryloyl chloride (IV) is reacted with 4-hydroxy benzaldehyde (V) to give 4-formylphenylmethacrylate (VI) which is then polymerized with the aid of an initiator in a solvent, followed by substituting the 4-formylphenyl groups with methanol or ethanol:

(reaction formula 3)

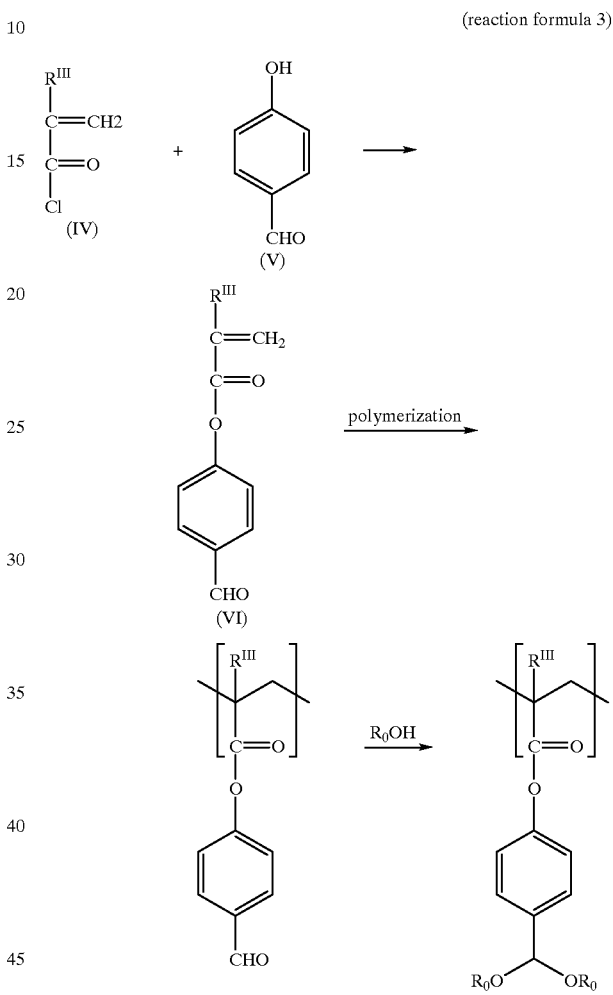

wherein $R^{III}$ and $R_0$ each is as defined above.

For initiating the polymerization reaction for the polymers of the general formulas I, II and III, ordinary initiators may be used, with preference given to 2,2-azobisisobutyronitrile (AIBN), acetylperoxide, laurylperoxide and t-butylperoxide. Also, ordinary solvents may be used for the polymerization. Preferably the solvent is selected from the group consisting of tetrahydrofuran, toluene, benzene, methylethyl ketone and dioxane.

Preferably, the polymerization of the polymers of the general formulas I and II is carried out at 50–90° C.

The 9-anthracene alkyl acrylate type monomers (I) used to prepare the polymers of the general formulas I and II, are novel compounds which can be prepared by the reaction of 9-anthracene alcohol with acryloyl chloride type compounds in a solvent, as illustrated in the following reaction formula 4:

(reaction formula 4)

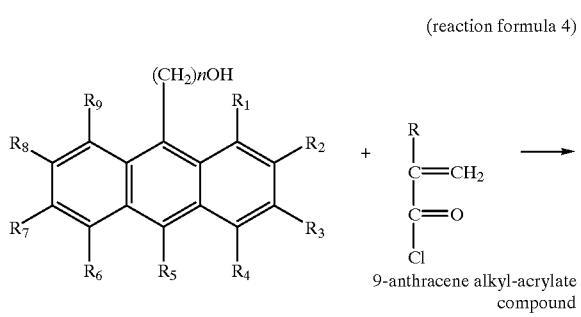

9-anthracene alkyl-acrylate compound wherein R, $R_1$ to $R_9$, and n each is as defined above. The hydroxyalkylacrylate type monomers (II) and methylmethacrylate monomers (III) used in the above reactions are commercially available, or they may be prepared using known preparation methods.

Also, the present invention pertains to an ARC composition which is based on a polymer mixture comprising the polymer of the general formula I or II and the polymer of the general formula III, in combination with at least one additive selected from the group consisting of the anthracene derivatives shown in Table 1, below.

TABLE 1

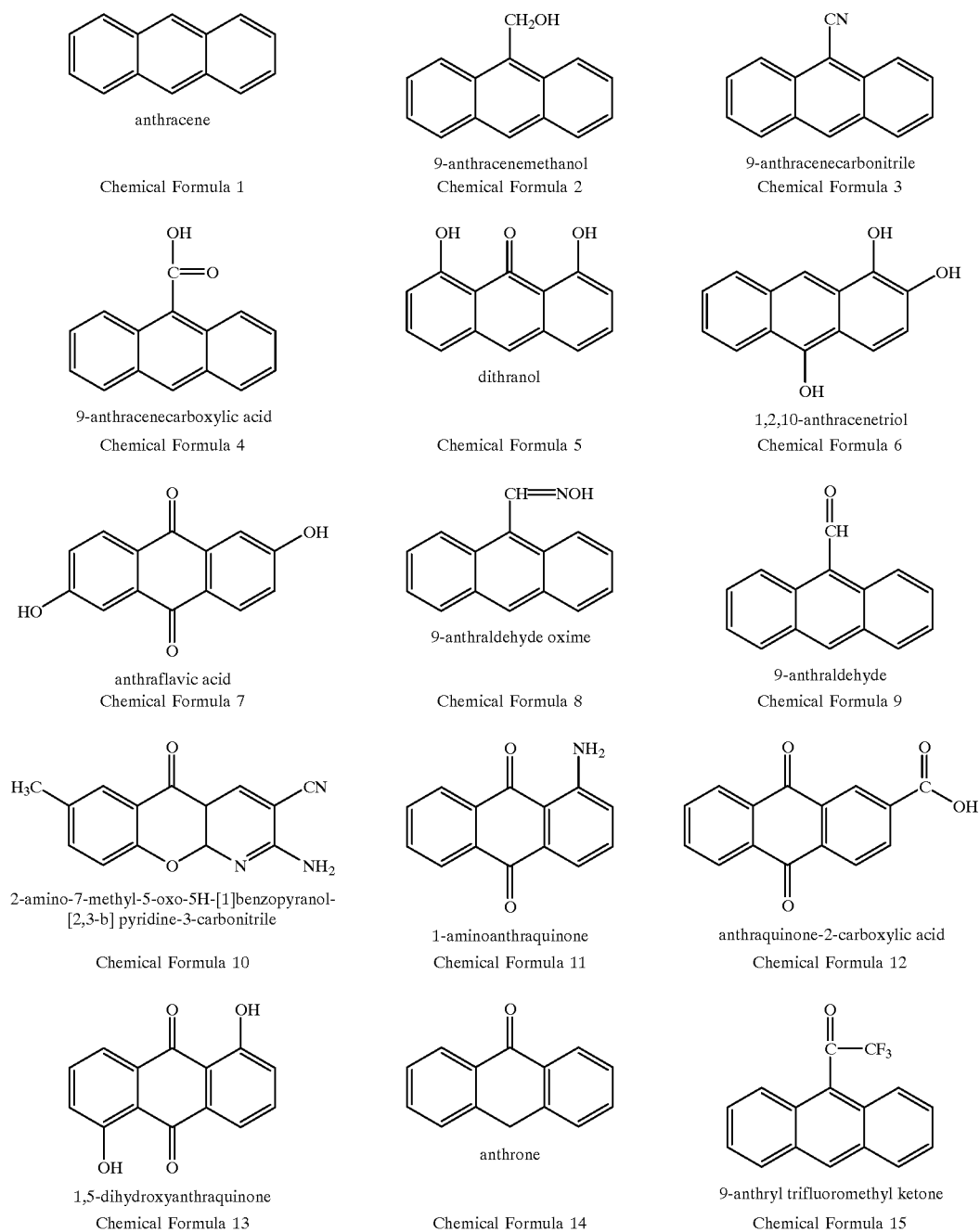

TABLE 1-continued

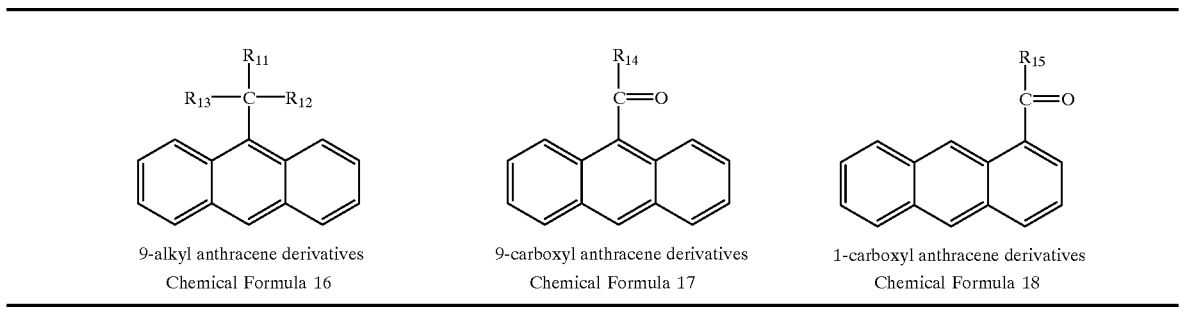

| 9-alkyl anthracene derivatives | 9-carboxyl anthracene derivatives | 1-carboxyl anthracene derivatives |
|---|---|---|
| Chemical Formula 16 | Chemical Formula 17 | Chemical Formula 18 |

In Table 1, $R_{11}$, $R_{12}$, $R_{13}$, $R_{14}$ and $R_{15}$ independently represent hydrogen, hydroxy, hydroxymethyl, or substituted or unsubstituted linear or branched $C_1$–$C_5$ alkyl, alkane, alkoxyalkyl or alkoxyalkane.

ARC compositions according to the present invention may be prepared by (i) dissolving a polymer of the general formula I or II and a polymer of general formula III in a solvent to form a solution; (ii) optionally adding a compound selected from Table 1 to said solution, at an amount of 0.1 to 30% by weight, and (iii) filtering the solution.

Ordinary organic solvents may be used in preparing the composition, with preference given to ethyl 3-ethoxypropionate, methyl 3-methoxy propionate, cyclohexanone and propylene methyletheracetate. The solvent is preferably used at an amount of 200 to 5000% by weight based on the total weight of the ARC resin polymers used.

In another aspect of the present invention, an ARC is formed from the coating composition described above. After being filtered, this coating composition may be applied on a wafer in a conventional manner and then "hard-baked" (i.e., heated to a temperature of 100–300° C. for 10–1000 seconds) to form a crosslinked ARC. Quality semiconductor devices can be fabricated using ARCs of the present invention, because this crosslinked structure of the ARC offers optically stable light exposure conditions when forming an image in the photosensitive layer.

It has been found that the ARCs of the present invention exhibit high performance in submicrolithographic processes using 248 nm KrF, 193 nm ArF and 157 nm $F_2$ lasers as light sources. The same was also true when 157 nm E-beams, EUV extreme ultraviolet) and ion beams are used as light sources.

A better understanding of the present invention may be obtained in light of following examples which are set forth to illustrate, but are not to be construed to limit, the present invention.

EXAMPLE I

Synthesis of Poly[9-anthracenemethylacrylate-(2-hydroxyethylacrylate)]binary Copolymer Synthesis of 9-Anthracenemethylacrylate 0.5 moles of 9-anthracene methanol and 0.5 moles of pyridine are dissolved in tetrahydrofuran and then, 0.5 moles of acryloyl chloride are added. After completion of the reaction, the product is filtered out and extracted with ethyl acetate. The extract is washed many times with distilled water and dried by distillation under vacuum, to give 9-anthracenemethylacrylate, represented by the following chemical formula 19. Yield 84%.

(chemical formula 19)

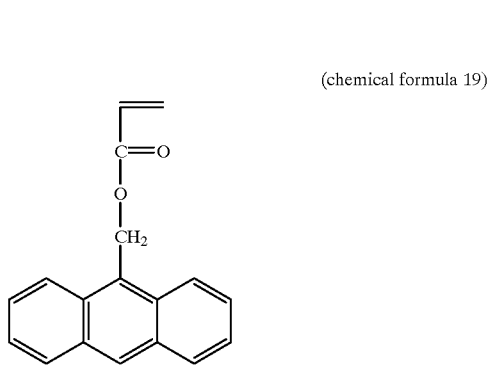

Synthesis of Poly[9-anthracenemethylacrylate-(2-hydroxyethylacrylate)]binary Copolymer In a 500 ml round-bottom flask are placed 0.5 moles of 9-anthracenemethylacrylate and 0.5 moles of 2-hydroxyethylacrylate. This mixture is added to 300 g of separately prepared tetrahydrofuran (THF) with stirring. Thereafter, in the presence of 0.1–3 g of 2,2'-azobisisobutyronitrile (AIBN), the reaction is subjected to polymerization at 60–75° C. for 5–20 hours in a nitrogen atmosphere. After completion of the polymerization, the solution is precipitated in ethyl ether or normal-hexane and the precipitate is filtered out and dried to produce a poly[9-anthracenemethylacrylate-(2-hydroxyethylacrylate)] copolymer, a polymer according to the present invention, represented by the following chemical formula 20, at a yield of 83%.

(chemical formula 20)

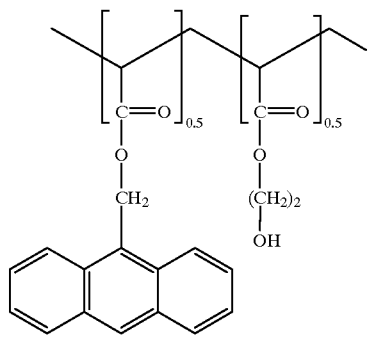

EXAMPLE II

Synthesis of Poly[9-anthracenemethylacrylate-(3-hydroxypropylacrylate)]binary Copolymer In a 500 ml round-bottom flask are placed 0.5 moles of the 9-anthracenemethylacrylate synthesized in Example I and 0.5 moles of 3-hydroxypropylacrylate. This mixture is added to 300 g of separately prepared THF with stirring. Thereafter, in the presence of 0.1–3 g of AIBN, the reaction is subjected to polymerization at 60–75° C. for 5–20 hours in a nitrogen atmosphere. After completion of the polymerization, the solution is precipitated in ethyl ether or normal-hexane and the precipitate is filtered out and dried to produce a poly[9-anthracenemethylacrylate-(3-hydroxypropylacrylate)] copolymer, a polymer according to the present invention, represented by the following chemical formula 21, at a yield of 82%.

(chemical formula 21)

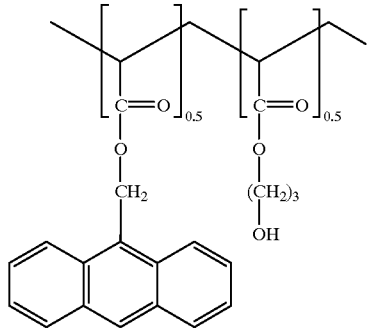

EXAMPLE III

Synthesis of Poly[9-anthracenemethylacrylate-(4-hydroxybutylacrylate)] Copolymer In a 500 ml round-bottom flask are placed 0.5 moles of 9-anthracenemethylacrylate and 0.5 moles of 4-hydroxybutylacrylate. This mixture is added to 300 g of separately prepared THF with stirring. Thereafter, in the presence of 0.1–3 g of AIBN, the reaction is subjected to polymerization at 60–75° C. for 5–20 hours in a nitrogen atmosphere. After completion of the polymerization, the solution is precipitated in ethyl ether or normal-hexane and the precipitate is filtered out and dried to produce a poly[9-anthracenemethylacrylate-(4-hydroxybutylacrylate)] copolymer, a polymer according to the present invention, represented by the following chemical formula 22. Yield 81%.

(chemical formula 22)

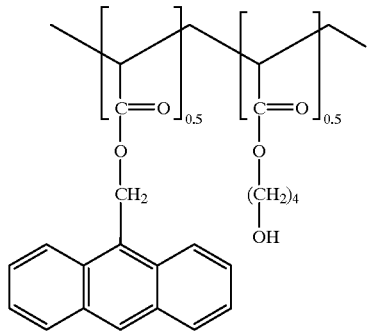

EXAMPLE IV

Synthesis of Poly[9-anthracenemethylmethacrylate-(2-hydroxyethylacrylate)]binary Copolymer
Synthesis of 9-Anthracenemethylmethacrylate 0.5 moles of 9-anthracene methanol and 0.5 moles of pyridine are dissolved in THF and then, 0.5 moles of methacryloyl chloride are added. After completion of the reaction, the product is filtered out and extracted with ethyl acetate. The extract is washed many times with distilled water and dried by distillation under vacuum, to give 9-anthracenemethylmethacrylate, represented by the following chemical formula 23. Yield 83%.

(chemical formula 23)

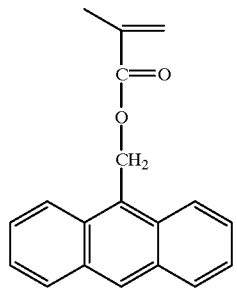

Synthesis of Poly[9-anthracenemethylmethacrylate-(2-hydroxyethylacrylate)]binary Copolymer In a 500 ml round-bottom flask are placed 0.5 moles of 9-anthracenemethylmethacrylate and 0.5 moles of 2-hydroxyethylacrylate. This mixture is added to 300 g of separately prepared THF with stirring. Thereafter, in the presence of AIBN, the reaction is subjected to polymerization at 60–75° C. for 5–20 hours in a nitrogen atmosphere. After completion of the polymerization, the solution is precipitated in ethyl ether or normal-hexane and the precipitate is filtered and dried to produce a poly[9-anthracenemethylmethacrylate-(2-hydroxyethylacrylate)] copolymer, a resin according to the present invention, represented by the following chemical formula 24, at a yield of 79%.

(chemical formula 24)

EXAMPLE V

Synthesis of Poly[9-anthracenemethylmethacrylate-(3-hydroxypropylacrylate)]binary Copolymer In a 500 ml round-bottom flask are placed 0.5 moles of the 9-anthracenemethylmethacrylate synthesized in Example IV and 0.5 moles of 3-hydroxypropylacrylate. This mixture is added to 300 g of separately prepared THF with stirring. Thereafter, in the presence of 0.1–3 g of AIBN, the reaction is subjected to polymerization at 60–75° C. for 5–20 hours in a nitrogen atmosphere. After completion of the polymerization, the solution is precipitated in ethyl ether or normal-hexane and the precipitate is filtered and dried to produce a poly[9-anthracenemethylmethacrylate-(2-hydroxypropylacrylate)] copolymer, a polymer according to the present invention, represented by the following chemical formula 25. Yield 81%.

(chemical formula 25)

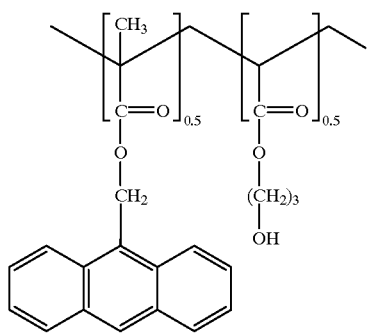

EXAMPLE VI

Synthesis of Poly[9-anthracenemethylmethacrylate-(4-hydroxybutylacrylate)]binary Copolymer In a 500 ml round-bottom flask are placed 0.5 moles of the 9-anthracenemethylacrylate synthesized in Example IV and 0.5 moles of 4-hydroxybutylacrylate. This mixture is added to 300 g of separately prepared THF with stirring. Thereafter, in the presence of 0.1–3 g of AIBN, the reaction is subjected to polymerization at 60–75° C. for 5–20 hours in a nitrogen atmosphere. After completion of the polymerization, the solution is precipitated in ethyl ether or normal-hexane and the precipitate is filtered and dried to produce a poly[9-anthracenemethylmethacrylate-(4-hydroxybutylacrylate)] copolymer, a polymer according to the present invention, represented by the following chemical formula 26, at a yield of 81%.

(chemical formula 26)

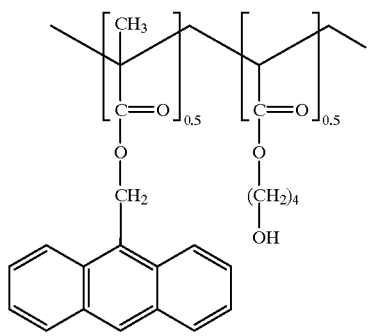

EXAMPLE VII

Synthesis of Poly[9-anthracenemethylacrylate-(2-hydroxyethylacrylate)-methylmethacrylate]ternary Copolymer In a 500 ml round-bottom flask are placed 0.3 moles of 9-anthracenemethylacrylate, 0.5 moles of 2-hydroxyethylacrylate and 0.2 moles of methylmethacrylate. This mixture is added to 300 g of separately prepared THF with stirring, after which, in the presence of 0.1–3 g of AIBN, the reaction was subjected to polymerization at 60–75° C. for 5–20 hours in a nitrogen atmosphere. After completion of the polymerization, the solution is precipitated in ethyl ether or normal-hexane and the precipitate is filtered and dried to produce a poly[9-anthracenemethylacrylate-(2-hydroxyethyl)-methylmethacrylate] copolymer, a polymer according to the present invention, represented by the following chemical formula 27. Yield 80%.

(chemical formula 27)

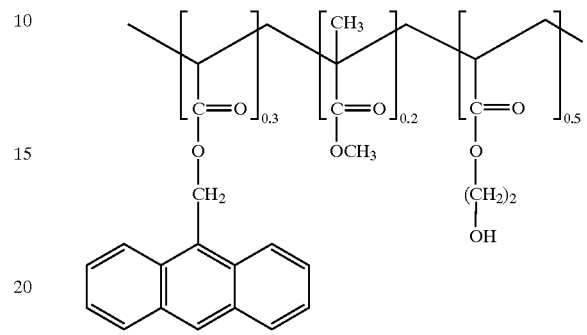

EXAMPLE VIII

Synthesis of Poly[9-anthracenemethylacrylate-(3-hydroxypropylacrylate)-methylmethacrylate]ternary Copolymer In a 500 ml round-bottom flask are placed 0.3 moles of 9-anthracenemethylacrylate, 0.5 moles of 3-hydroxypropylacrylate and 0.2 moles of methylmethacrylate. This mixture is added to 300 g of separately prepared THF with stirring, after which, in the presence of 0.1–3 g of AIBN, the reaction was subjected to polymerization at 60–75° C. for 5–20 hours in a nitrogen atmosphere. After completion of the polymerization, the solution is precipitated in ethyl ether or normal-hexane and the precipitate is filtered and dried to produce a poly[9-anthracenemethylacrylate-(3-hydroxypropyl)-methylmethacrylate] copolymer, a polymer according to the present invention, represented by the following chemical formula 28, at a yield of 82%.

(chemical formula 28)

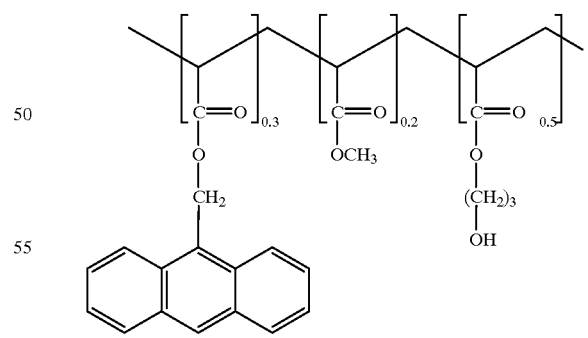

EXAMPLE IX

Synthesis of Poly[9-anthracenemethylacrylate-(4-hydroxybutylacrylate)-methylmethacrylate]ternary Copolymer In a 500 ml round-bottom flask are placed 0.3 moles of 9-anthracenemethylacrylate, 0.5 moles of 4-hydroxybutylacrylate and 0.2 moles of methylmethacrylate. This mixture is added to 300 g of separately prepared THF with stirring, after which, in the presence of 0.1–3 g of AIBN, the reaction is subjected to polymerization at 60–75° C. for 5–20 hours in a nitrogen atmosphere. After completion of the polymerization, the solution is precipitated in ethyl ether or normal-hexane and the precipitate is filtered and dried to produce a poly[9-anthracenemethylacrylate-(4-hydroxybutyl)-methylmethacrylate] copolymer, a polymer according to the present invention, represented by the following chemical formula 29. Yield 81%.

(chemical formula 29)

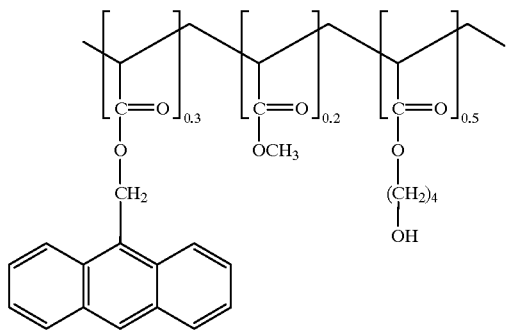

EXAMPLE X

Synthesis of Poly[9-anthracenemethylmethacrylate-(2-hydroxyethylacrylate)-methylmethacrylate] ternary Copolymer In a 500 ml round-bottom flask are placed 0.3 moles of the 9-anthracenemethylmethacrylate synthesized in Example IV, 0.5 moles of 2-hydroxyethylacrylate and 0.2 moles of methylmethacrylate. This mixture is added to 300 g of separately prepared THF with stirring, after which, in the presence of 0.1–3 g of AIBN, the reaction is subjected to polymerization at 60–75° C. for 5–20 hours in a nitrogen atmosphere. After completion of the polymerization, the solution is precipitated in ethyl ether or normal-hexane and the precipitate is filtered and dried to produce a poly[9-anthracenemethylmethacrylate-(2-hydroxyethyl)-methylmethacrylate] copolymer, a polymer according to the present invention, represented by the following chemical formula 30. Yield 82%.

(chemical formula 30)

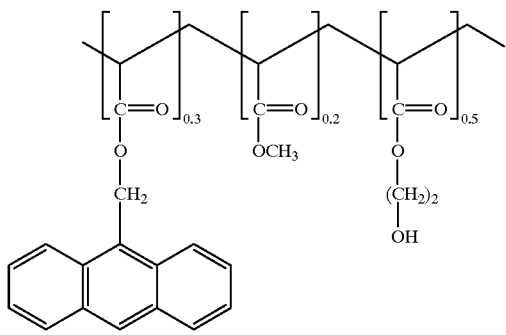

EXAMPLE XI

Synthesis of Poly[9-anthracenemethylmethacrylate-(3-hydroxypropylacrylate)-methylmethacrylate] ternary Copolymer In a 500 ml round-bottom flask are placed 0.3 moles of the 9-anthracenemethylacrylate synthesized in Example IV, 0.5 moles of 3-hydroxypropylacrylate and 0.2 moles of methylmethacrylate. This mixture is added to 300 g of separately prepared THF with stirring, after which, in the presence of 0.1–3 g of AIBN, the reaction is subjected to polymerization at 60–75° C. for 5–20 hours in a nitrogen atmosphere. After completion of the polymerization, the solution is precipitated in ethyl ether or normal-hexane and the precipitate is filtered and dried to produce a poly[9-anthracenemethylmethacrylate-(3-hydroxypropyl)-methylmethacrylate] copolymer, a polymer according to the present invention, represented by the following chemical formula 31, at a yield of 81%.

(chemical formula 31)

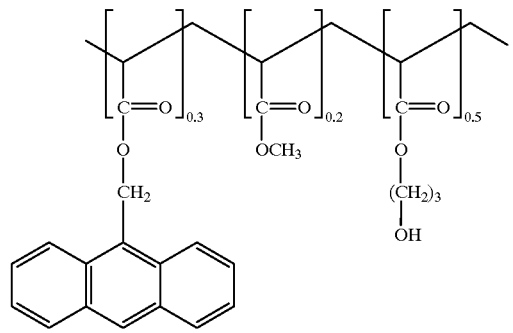

EXAMPLE XII

Synthesis of Poly[9-anthracenemethylmethacrylate-(4-hydroxybutylacrylate)-methylmethacrylate] ternary Copolymer In a 500 ml round-bottom flask are placed 0.3 moles of the 9-anthracenemethylacrylate synthesized in Example IV, 0.5 moles of 4-hydroxybutylacrylate and 0.2 moles of methylmethacrylate. This mixture is added to 300 g of separately prepared THF with stirring, after which, in the presence of 0.1–3 g of AIBN, the reaction is subjected to polymerization at 60–75° C. for 5–20 hours in a nitrogen atmosphere. After completion of the polymerization, the solution is precipitated in ethyl ether or normal-hexane and the precipitate is filtered and dried to produce a poly[9-anthracenemethylmethacrylate-(4-hydroxybutyl)-methylmethacrylate] copolymer, a polymer according to the present invention, represented by the following chemical formula 32. Yield 80%.

(chemical formula 32)

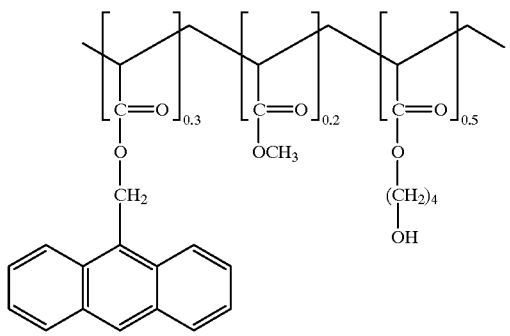

(chemical formula 34)

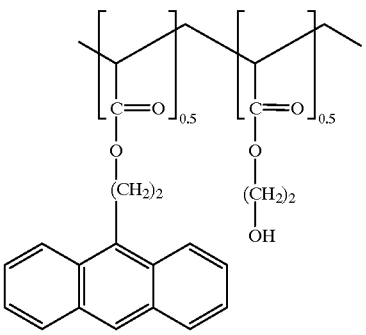

EXAMPLE XIII

Synthesis of Poly[9-anthraceneethylacrylate-(2-hydroxyethylacrylate)]binary Copolymer Synthesis of 9-Anthraceneethylacrylate 0.5 moles of 9-anthracene ethanol and 0.5 moles of pyridine are dissolved in THF and then, 0.5 moles of acryloyl chloride are added. After completion of the reaction, the product is filtered out and extracted with ethyl acetate. The extract is washed many times with distilled water and dried by distillation under vacuum, to give 9-anthracenemethylacrylate, represented by the following chemical formula 33. Yield 80%.

(chemical formula 33)

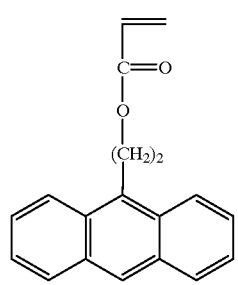

Synthesis of Poly[9-anthraceneethylacrylate-(2-hydroxyethylacrylate)] Copolymer

In a 500 ml round-bottom flask are placed 0.5 moles of 9-anthraceneethylacrylate and 0.5 moles of 2-hydroxyethylacrylate. This mixture is added to 300 g of separately prepared THF with stirring. Thereafter, in the presence of 0.1–3 g of AIBN, the reaction is subjected to polymerization at 60–75° C. for 5–20 hours in a nitrogen atmosphere. After completion of the polymerization, the solution is precipitated in ethyl ether or normal-hexane and the precipitate is filtered out and dried to produce a poly[9-anthraceneethylacrylate-(2-hydroxyethylacrylate)] copolymer, a resin according to the present invention, represented by the following chemical formula 34, at a yield of 82%.

EXAMPLE XIV

Synthesis of Poly[9-anthraceneethylacrylate-(3-hydroxypropylacrylate)]binary Copolymer In a 500 ml round-bottom flask are placed 0.5 moles of the 9-anthraceneethylacrylate synthesized in Example XIII and 0.5 moles of 3-hydroxypropylacrylate. This mixture is added to 300 g of separately prepared THF with stirring. Thereafter, in the presence of 0.1–3 g of AIBN, the reaction is subjected to polymerization at 60–75° C. for 5–20 hours in a nitrogen atmosphere. After completion of the polymerization, the solution is precipitated in ethyl ether or normal-hexane and the precipitate is filtered out and dried to produce a poly[9-anthraceneethylacrylate-(3-hydroxypropylacrylate)] copolymer, a polymer according to the present invention, represented by the following chemical formula 35, at a yield of 81%.

(chemical formula 35)

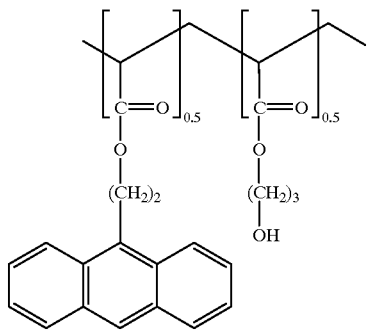

EXAMPLE XV

Synthesis of Poly[9-anthraceneethylacrylate-(4-hydroxybutylacrylate)] Copolymer

In a 500 ml round-bottom flask are placed 0.5 moles of 9-anthraceneethylacrylate and 0.5 moles of 4-hydroxybutylacrylate. This mixture is added to 300 g of separately prepared THF with stirring. Thereafter, in the presence of 0.1–3 g of AIBN, the reaction solution is subjected to polymerization at 60–75° C. for 5–20 hours in a nitrogen atmosphere. After completion of the polymerization, the solution is precipitated in ethyl ether or normal-hexane and the precipitate is filtered and dried to produce a poly[9-anthraceneethylacrylate-(4- hydroxybutylacrylate)] copolymer, a polymer according to the present invention, represented by the following chemical formula 36. Yield 80%.

(chemical formula 36)

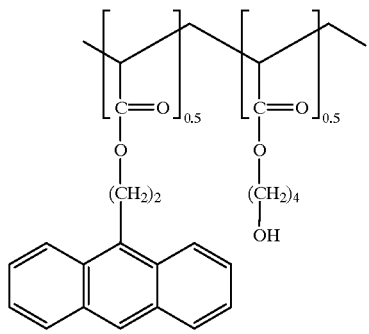

EXAMPLE XVI

Synthesis of Poly[4-(1,1-dimethoxymethyl) phenylmethacrylate)

Synthesis of poly[4-formylphenylmethacrylate]

In a 300 ml round-bottom flask, 31.3 g of (0.3 moles) of methacryloyl are completely dissolved in 200 g of THF by stirring and 26 g of pyridine are added. To this solution 36.6 g (0.3 moles) of 4-hydroxybenzaldehyde are added dropwise, after which these reactants are allowed to react for 24 hours or longer. The product solution is washed with deionized water to separate an aqueous layer from which the desired compound is extracted and dried.

0.4 moles of the 4-formylphenylmethacrylate thus obtained are placed, together with 300 g of THF, in a 500 ml round-bottom flask and 0.1–3 g of AIBN are added thereto with stirring. Polymerization is conducted at 60–75° C. for 5–20 hours in a nitrogen atmosphere. After completion of the polymerization, the solution is precipitated in ethyl ether or normal hexane and the precipitate is filtered and dried to provide a poly[4-formylphenylmethacrylate] polymer at a yield of 80%.

Synthesis of poly[4-(1,1-dimethoxymethyl) phenylmethacrylate]

In a 400 ml Erlenmeyer flask are placed 15 g of the polymer obtained above and 200 ml of THF and then, 100 g of methanol are added, together with 0.5 g of HCl, after which these reactants are allowed to react at 60° C. for about 12 hours. The product solution is precipitated in ethyl ether or normal hexane and the precipitate is filtered and dried to give poly[4-(1,1-dimethoxymethyl)phenylmethacrylate], a polymer according to the present invention, represented by the following chemical formula 37. Yield 82%.

(chemical formula 37)

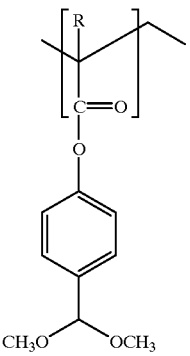

EXAMPLE XVII

Synthesis of Poly[4-(1,1-diethoxymethyl) phenylmethacrylate]

In a 400 ml Erlenmeyer flask are placed 15 g of the poly[4-formylmethacrylate synthesized in Example XVI and 200 ml of THF and then, 150 g of ethanol are added, together with 0.5 g of HCl, after which these reactants are allowed to react at 60° C. for about 12 hours. The product solution is precipitated in ethyl ether or normal hexane and the precipitate is filtered and dried to give poly[4-(1,1-diethoxymethyl)phenylmethacrylate], a resin according to the present invention, represented by the following chemical formula 38. Yield 80%.

(chemical formula 38)

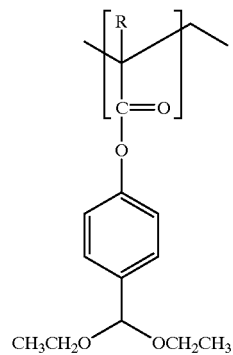

EXAMPLE XVIII

Preparation of Arc

A polymer prepared in each of Examples I to XV and a polymer prepared in Example XVI or XVII are dissolved in propyleneglycol methylether acetate (PGMEA). This solution, alone or in combination with 0.1–30% by weight of at least one additive selected from the compounds of the chemical formulas 1 to 18 in Table 1, is filtered, coated on a wafer, and hard-baked at 100–300° C. for 10–1,000 sec to form an ARC. A photosensitive material may be applied on the ARC thus formed and imaged to ultrafine patterns in the conventional manner.

As described hereinbefore, the ARC of the present invention, which is obtained from a mixture comprising a polymer of the general formula I or II and a polymer of the general formula III, alone or in combination with an additive of chemical formulas 1 to 18 in Table 1, contains chromophore substituents sufficient to exhibit absorbance at the wavelengths useful for submicrolithography.

Particularly, the ARC of the present invention provides maximal crosslinking reaction efficiency and storage stability. The ARC polymer resins of the present invention show superior solubility in all hydrocarbon solvents, but are of such high solvent resistance after hard baking that they are not dissolved in any solvent at all. These advantages allow the resins to be coated without any problem, and the resulting coating prevents undercutting and footing problems which may occur when forming images on photosensitive materials. Furthermore, coatings made of the acrylate polymers of the present invention are higher in etch rate than photosensitive films, improving the etch selection ratio therebetween.

Thus, ARCs of the present invention can play an excellent role in forming ultrafine patterns. For example, it can prevent the back reflection of light from lower layers or the surface of the semiconductor element, as well as eliminate the standing waves caused by light and the thickness changes in the photoresist layer itself, during a submicrolithographic process using a 248 nm KrF, 193 nm ArF or 157 nm F2 laser. This results in the stable formation of ultrafine patterns suitable for 64M, 256M, 1 G, 4 G and 16 G DRAM semiconductor devices and a great improvement in the production yield.

The present invention has been described in an illustrative manner, and it is to be understood the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A polymer represented by the following general formula I:

(general formula I)

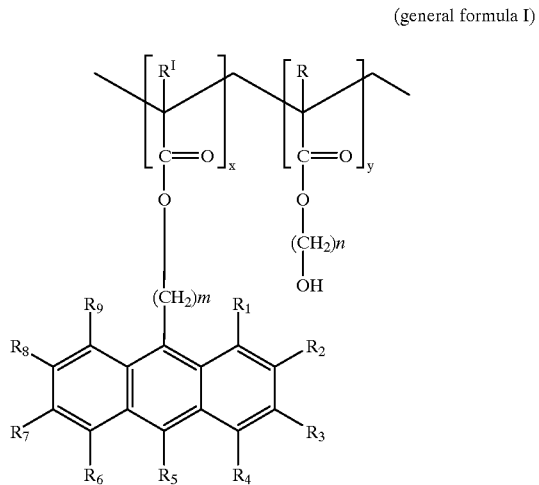

wherein,
R and $R^I$, which are the same or different, each represents hydrogen or —$CH_3$;
$R_1$ to $R_9$, which are the same or different, each represents methoxycarbonyl, carboxyl, or hydroxymethyl;
x and y each is a mole fraction in the range from 0.01 to 0.99; and
m is 1 or 2 and n is an integer of 2 to 4.

2. A polymer as set forth in claim 1, wherein $R^I$ is hydrogen; x and y each is 0.5; and m is 1 and n is 2.
3. A polymer as set forth in claim 1, wherein $R^I$ is hydrogen; x and y each is 0.5; and m is 1 and n is 3.
4. A polymer as set forth in claim 1, wherein $R^I$ is hydrogen; x and y each is 0.5; and m is 1 and n is 4.
5. A polymer as set forth in claim 1, wherein $R^I$ is —$CH_3$; x and y each is 0.5; and m is 1 and n is 2.
6. A polymer as set forth in claim 1, wherein $R^I$ is —$CH_3$; x and y each is 0.5; and m is 1 and n is 3.
7. A polymer as set forth in claim 1, wherein $R^I$ is —$CH_3$; x and y each is 0.5; and m is 1 and n is 4.
8. A polymer as set forth in claim 1, wherein $R^I$ is $CH_3$; x and y each is 0.5; and m is 1 and n is 2.
9. A polymer represented by the following general formula II:

(general formula II)

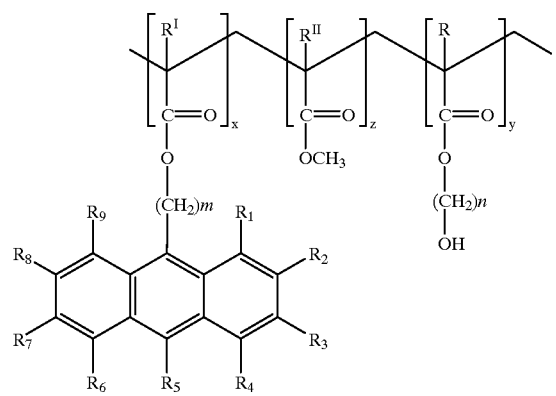

wherein,
R, $R^I$, and $R^{II}$, which are the same or different, each is hydrogen or —$CH_3$;
$R_1$ to $R_9$, which are the same or different, each represents hydrogen, hydroxy, methoxycarbonyl, carboxyl, hydroxymethyl, or a substituted or unsubstituted, linear or branched $C_1$–$C_6$ alkyl, alkane, alkoxyalkyl or alkoxyalkane;
x, y and z each is an mole fraction in the range from 0.01 to 0.99; and
m is 1 or 2 and n is an integer of 2 to 4.

10. A polymer as set forth in claim 9, wherein $R_1$–$R_9$ each is hydrogen; $R^I$ is hydrogen; x, y and z are 0.3, 0.5 and 0.2, respectively; and m is 1 and n is 2.
11. A polymer as set forth in claim 9, wherein $R_1$–$R_9$ each is hydrogen; $R_I$ is hydrogen; x, y and z are 0.3, 0.5 and 0.2, respectively; and m is 1 and n is 3.
12. A polymer as set forth in claim 9, wherein $R_1$–$R_9$ each is hydrogen; $R^I$ is hydrogen; x, y and z are 0.3, 0.5 and 0.2, respectively; and m is 1 and n is 4.
13. A polymer as set forth in claim 9, wherein $R_1$–$R_9$ each is hydrogen; $R^I$ is —$CH_3$; x, y and z are 0.3, 0.5 and 0.2, respectively; and m is 1 and n is 2.
14. A polymer as set forth in claim 9, wherein $R_1$–$R_9$ each is hydrogen; $R^I$ is —$CH_3$; x, y and z are 0.3, 0.5 and 0.2; and m is 1 and n is 3.
15. A polymer as set forth in claim 9, wherein $R_1$–$R_9$ each is hydrogen; $R^I$ is —$CH_3$; x, y and z are 0.3, 0.5 and 0.2, respectively; and m is 1 and n is 4.
16. A polymer represented by the following general formula I:

(general formula I)

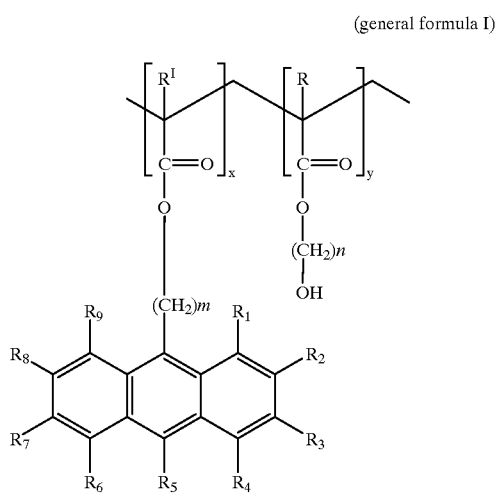

wherein,

R and R′, which are the same or different, each represents hydrogen or —CH$_3$;

R$_1$ to R$_9$, which are the same or different, each represents hydrogen, hydroxy, methoxycarbonyl, carboxyl, hydroxymethyl, or a substituted or unsubstituted, linear or branched C$_1$–C$_6$ alkyl, alkane, alkoxyalkyl or alkoxyalkane;

x and y each is a mole fraction in the range from 0.01 to 0.99; and m is 2 and n is an integer of 2 to 4.

17. A polymer as set forth in claim 16, wherein R$_1$–R$_9$ each is hydrogen; R′ is hydrogen; x and y each is 0.5; and n is 3.

18. A polymer as set forth in claim 16, wherein R$_1$–R$_9$ each is hydrogen; R′ is hydrogen; x and y each is 0.5; and n is 4.

19. A method for preparing a copolymer (III), which comprises reacting a 9-anthracene alkylacrylate type monomer (I) with a hydroxyalkylacrylate type monomer (II) in the presence of an initiator in a solvent, as shown in the following reaction formula 5:

(reaction formula 5)

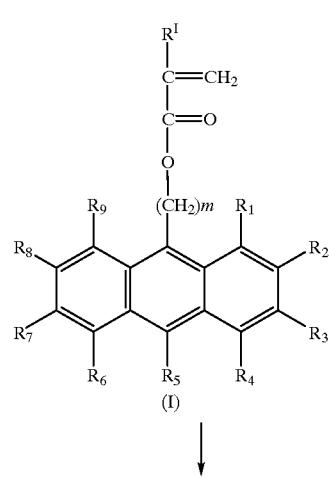

-continued

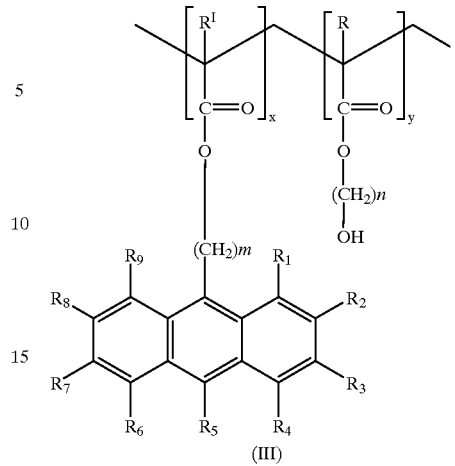

wherein, R; R$_1$ to R$_9$; and m and n have the meanings set forth in claim 1.

20. A method for preparing a copolymer (IV) which comprises reacting a 9-anthracene alkylacrylate type monomer (I), a hydroxyalkylacrylate type monomer (II) and methylmethacrylate (III) with each other in the presence of an initiator in a solvent, as shown in the following reaction formula 6:

(reaction formula 6)

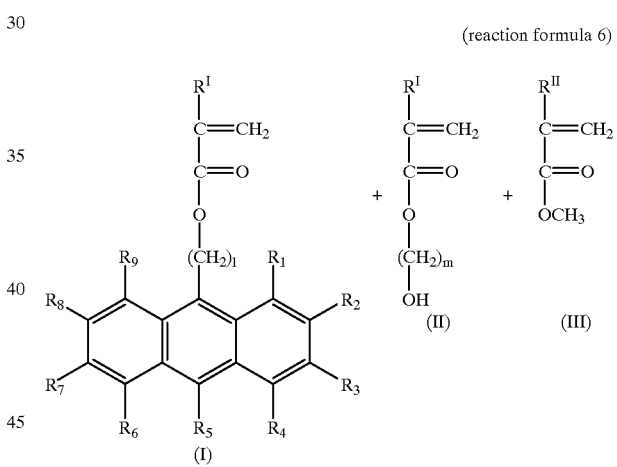

wherein,

R, $R^I$, and $R^{III}$,; R1 to R9; and m and n have the meanings set forth in claim 9.

21. A method as set forth in claim 19 or 20, wherein each of the monomers range, in mole fraction, from 0.01 to 0.99.

22. A method as set forth in claim 19 or 20, wherein the initiator is selected from the group consisting of 2,2-azobisisobutyronitrile, acetylperoxide, laurylperoxide, and t-butylperoxide.

23. A method as set forth in claim 19 or 20, wherein the solvent is selected from the group consisting of tetrahydrofuran, toluene, benzene, methylethyl ketone and dioxane.

24. A method as set forth in claim 19 or 20, wherein the polymerization is carried out at a temperature of 50–90° C.

25. A method for preparing a copolymer which comprises polymerizing formylphenylmethacrylate to form a polymer and then reacting said polymer with methanol or ethanol.

26. An anti-reflective coating composition comprising a polymer of claim 1, 9 or 16.

27. An anti-reflective coating composition as set forth in claim 26, further comprising an anthracene derivative.

28. An anti-reflective coating composition as set forth in claim 27, wherein the anthracene derivative is selected from the group consisting of anthracene, 9-anthracene methanol, 9-anthracene carbonitrile, 9-anthracene carboxylic acid, dithranol, 1,2,10-anthracenetriol, anthraflavic acid, 9-anthraldehyde oxime, 9-anthraldehyde, 2-amino-7-methyl-5-oxo-5H-[1]-benzopyrano[2,3-b]pyridine-3-carbonitrile, 1-aminoanthraquinone, anthraquinone-2-carboxylic acid, 1,5-dihydroxyanthraquinone, anthrone, 9-anthryl trifluoromethyl ketone, 9-alkylanthracene derivatives represented by the following chemical formula 16, 9-carboxyl anthracene derivatives represented by the following chemical formula 17, 1-carboxyl anthracene derivatives represented by the following chemical formula 18, and the combination thereof:

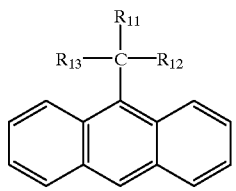

(chemical formula 16)

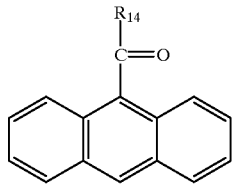

(chemical formula 17)

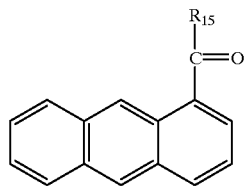

(chemical formula 18)

wherein, $R_{11}$, $R_{12}$, $R_{13}$, $R_{14}$ and $R_{15}$, which are the same or different, each represents —H, —OH, —$CH_3$, —$CH_2OH$, —$(CH_2)pCH_3$ wherein p is an integer of 1 to 3, or a substituted or unsubstituted, linear or branched alkyl, alkane, alkoxyalkyl or alkoxyalkane containing 1–5 carbon atoms.

29. A method for preparing an anti-reflective coating composition, which comprises:

dissolving in an organic solvent a polymer of claim 9 or a polymer selected from formula I and formula II:

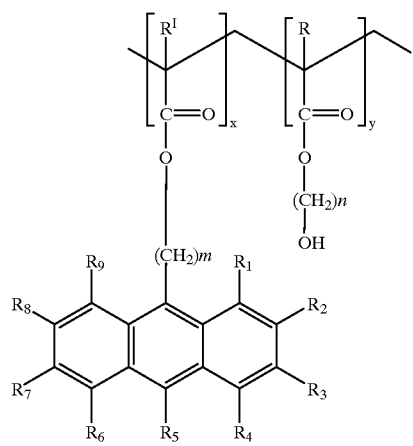

(formula I)

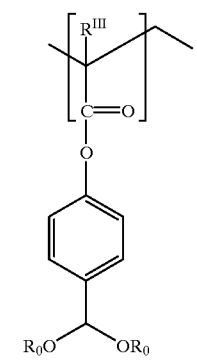

(formula II)

wherein, $R^{III}$ is hydrogen or —$CH_3$ and $R_0$ is —$CH_3$ or —$CH_2CH_3$, R and $R^I$, which are the same or different, each represents hydrogen or —$CH_3$; $R_1$ to $R_9$, which are the same or different, each represents hydrogen, hydroxy, methoxycarbonyl, carboxyl, hydroxymethyl, or a substituted or unsubstituted, linear or branched $C_1$–$C_6$ alkyl, alkane, alkoxyalkyl or alkoxyalkane; x and y each is a mole fraction in the range from 0.01 to 0.99; and m is 1 or 2 and n is an integer of 2 to 4; and then adding thereto, an anthracene derivative additive selected from the group consisting of anthracene, 9-anthracene methanol, 9-anthracene carbonitrile, 9-anthracene carboxylic acid, dithranol, 1,2,10-anthracenetriol, anthraflavic acid, 9-anthraldehyde oxime, 9-anthraldehyde, 2-amino-7-methyl-5-oxo-5H-[1]-benzopyrano[2,3-b]pyridine-3-carbonitrile, 1-aminoanthraquinone, anthraquinone-2-carboxylic acid, 1,5-dihydroxyanthraquinone, anthrone, 9-anthryl trifluoromethyl ketone, 9-alkylanthracene derivatives of the following chemical formula 16, 9-carboxyl anthracene derivatives of the following chemical formula 17, 1-carboxyl anthracene derivatives of the following chemical formula 18, and combinations thereof.

(chemical formula 16)

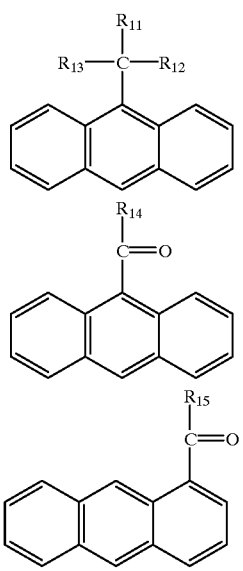

(chemical formula 17)

(chemical formula 18)

wherein, $R_{11}$, $R_{12}$, $R_{13}$, $R_{14}$ and $R_{15}$, which are the same or different, each represents —H, —OH, —CH$_3$, —CH$_2$OH, —(CH$_2$)pCH$_3$ wherein p is an integer of 1 to 3, or a substituted or unsubstituted, linear or branched alkyl, alkane, alkoxyalkyl or alkoxyalkane containing 1–5 carbon atoms.

30. A method as set forth in claim 29, wherein the anthracene derivative additive is used at an amount of 0.1 to 30% by weight.

31. A method as set forth in claim 29, wherein the organic solvent is selected from the group consisting of ethyl 3-ethoxypropionate, methyl 3-ethoxypropionate, cyclohexanone, and propyleneglycolmethyl ether acetate.

32. An anti-reflective coating composition, comprising (i) either a polymer of claim 16 or a polymer represented by the following general formula I:

(general formula I)

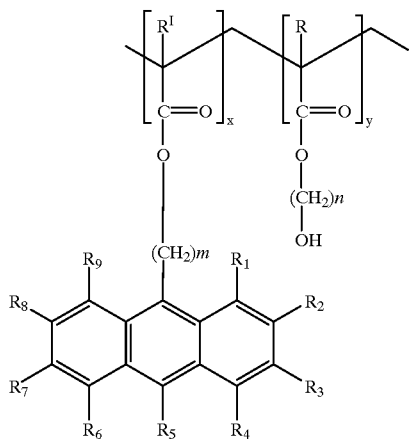

wherein, R and R', which are the same or different, each represents hydrogen or —CH$_3$; $R_1$ to $R_9$, which are the same or different, each represents hydrogen, hydroxy, methoxycarbonyl, carboxyl, hydroxymethyl, or a substituted or unsubstituted, linear or branched $C_1$–$C_6$ alkyl, alkane, alkoxyalkyl or alkoxyalkane; x and y each is a mole fraction in the range from 0.01 to 0.99; and m is 1 or 2 and n is an integer of 2 to 4; and (ii) a polymer of the formula:

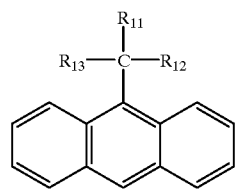

wherein, $R^{III}$ is hydrogen or —CH$_3$ and $R_0$ is —CH$_3$ or —CH$_2$CH$_3$.

33. An anti-reflective coating composition as set forth in claim 32, further comprising an anthracene derivative.

34. An anti-reflective coating composition as set forth in claim 33, wherein the anthracene derivative is selected from the group consisting of anthracene, 9-anthracene methanol, 9-anthracene carbonitrile, 9-anthracene carboxylic acid, dithranol, 1,2,10-anthracenetriol, anthraflavic acid, 9-anthraldehyde oxime, 9-anthraldehyde, 2-amino-7-methyl-5-oxo-5H-[1]-benzopyrano[2,3-b]pyridine-3-carbonitrile, 1-aminoanthraquinone, anthraquinone-2-carboxylic acid, 1,5-dihydroxyanthraquinone, anthrone, 9-anthryl trifluoromethyl ketone, 9-alkylanthracene derivatives of the following chemical formula 16, 9-carboxyl anthracene derivatives of the following chemical formula 17, 1-carboxyl anthracene derivatives of the following chemical formula 18, and combinations thereof:

(chemical formula 16)

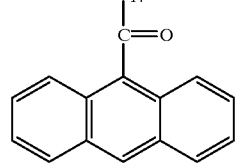

(chemical formula 17)

(chemical formula 18)

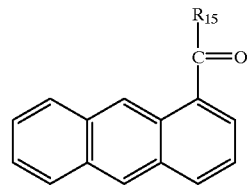

wherein, $R_{11}$, $R_{12}$, $R_{13}$, $R_{14}$ and $R_{15}$, which are the same or different, each represents —H, —OH, —CH$_3$, —CH$_2$OH, —(CH$_2$)pCH$_3$ wherein p is an integer of 1 to 3, or a substituted or unsubstituted, linear or branched alkyl, alkane, alkoxyalkyl or alkoxyalkane containing 1–5 carbon atoms.

35. A method for preparing an anti-reflective coating composition, which comprises:
dissolving in an organic solvent a mixture of: (i) a polymer of, claim 9 or a polymer represented by the following general formula I:

(general formula I)

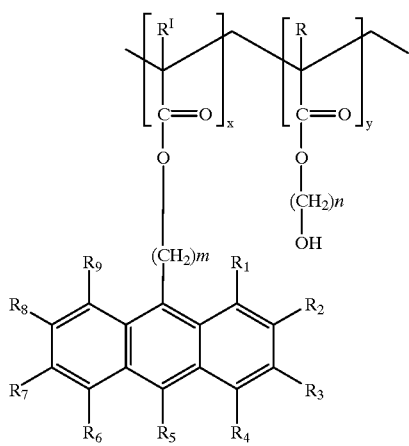

wherein, R and R', which are the same or different, each represents hydrogen or —CH$_3$; R$_1$ to R$_9$, which are the same or different, each represents hydrogen, hydroxy, methoxycarbonyl, carboxyl, hydroxymethyl, or a substituted or unsubstituted, linear or branched C$_1$–C$_6$ alkyl, alkane, alkoxyalkyl or alkoxyalkane; x and y each is a mole fraction in the range from 0.01 to 0.99; and m is 1 or 2 and n is an integer of 2 to 4; and (ii) a polymer of the formula:

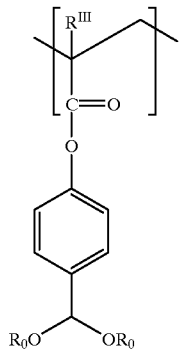

wherein, R$^{III}$ is hydrogen or —CH$_3$ and R$_0$ is —CH$_3$ or —CH$_2$CH$_3$ and then;

adding thereto an anthracene derivative additive selected from the group consisting of anthracene, 9-anthracene methanol, 9-anthracene carbonitrile, 9-anthracene carboxylic acid, dithranol, 1,2,10-anthracenetriol, anthraflavic acid, 9-anthraldehyde oxime, 9-anthraldehyde, 2-amino-7-methyl-5-oxo-5H-[1]-benzopyrano[2,3-b]pyridine-3-carbonitrile, 1-aminoanthraquinone, anthraquinone-2-carboxylic acid, 1,5-dihydroxyanthraquinone, anthrone, 9-anthryl trifluoromethyl ketone, 9-alkylanthracene derivatives of the following chemical formula 16, 9-carboxyl anthracene derivatives of the following chemical formula 17, 1-carboxyl anthracene derivatives of the following chemical formula 18, and combinations thereof (chemical formula 16)

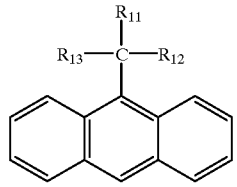

(chemical formula 17)

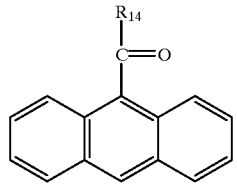

(chemical formula 18)

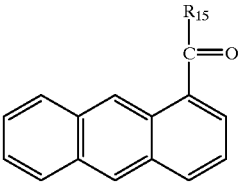

wherein, R$_{11}$, R$_{12}$, R$_{13}$, R$_{14}$ and R$_{15}$, which are the same or different, each represents —H, —OH, —CH$_3$, —CH$_2$OH, —(CH$_2$)pCH$_3$ wherein p is an integer of 1 to 3, or a substituted or unsubstituted, linear or branched alkyl, alkane, alkoxyalkyl or alkoxyalkane containing 1–5 carbon atoms.

36. A method as set forth in claim 35, wherein the anthracene derivative additive is used at an amount of 0.1 to 30% by weight.

37. A method as set forth in claim 35, wherein the organic solvent is selected from the group consisting of ethyl 3-ethoxypropionate, methyl 3-ethoxypropionate, cyclohexanone, and propyleneglycolmethyl ether acetate.

38. A method for forming an anti-reflective coating, in which an anti-reflective coating composition of claim 27, 32 or 33 is coated on a wafer and the wafer is subjected to hard baking at 80–300° C.

39. A semiconductor device, fabricated by using an anti-reflective coating of claim 27, 32 or 33.

40. A method for forming an anti-reflective coating, in which an anti-reflective coating composition of claim 26 is coated on a wafer and the wafer is subjected to hard baking at 80–300° C.

41. A semiconductor device, fabricated by using an anti-reflective coating of claim 26.

* * * * *

UNITED STATES PATENT AND TRADEMARK OFFICE
CERTIFICATE OF CORRECTION

PATENT NO. : 6,368,768 B1
DATED : April 9, 2002
INVENTOR(S) : Min-Ho Jung, Sung-Eun Hong and Ki-Ho Baik It is certified that error appears in the above-identified patent and that said Letters Patent is hereby corrected as shown below:

Title page,
Item [57], ABSTRACT,
General Formula II should read --

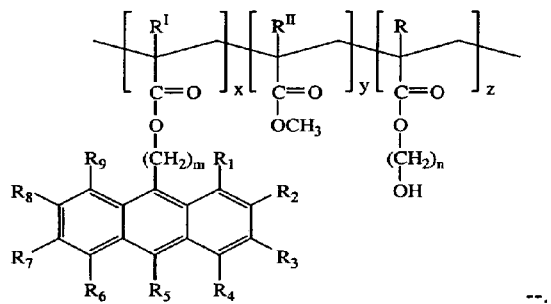

--.

Column 3,
Lines 30-45, the General Formula I should read --

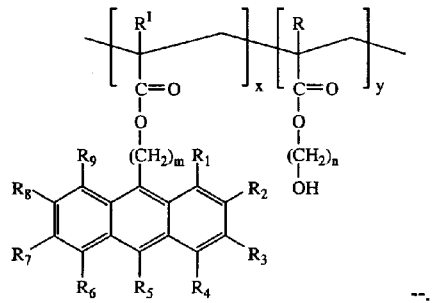

--.

Lines 50-65, the General Formula II should read --

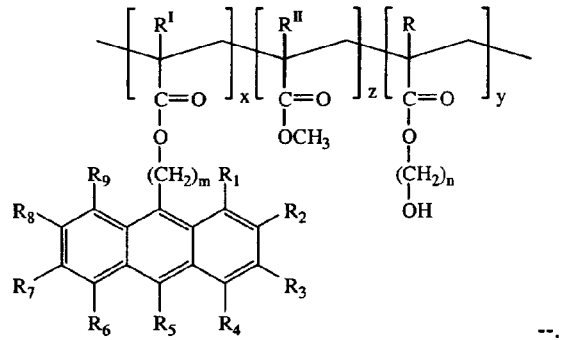

--.

UNITED STATES PATENT AND TRADEMARK OFFICE
CERTIFICATE OF CORRECTION

PATENT NO. : 6,368,768 B1
DATED : April 9, 2002
INVENTOR(S) : Min-Ho Jung, Sung-Eun Hong and Ki-Ho Baik It is certified that error appears in the above-identified patent and that said Letters Patent is hereby corrected as shown below:

Column 5,
Lines 1-19, the chemical formula should read --

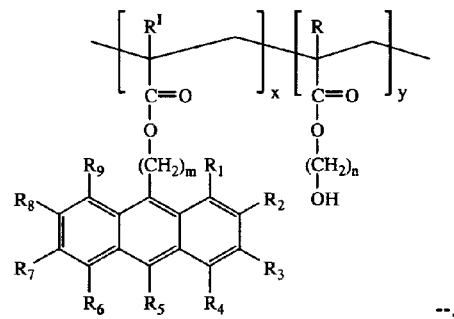

--.

Lines 50-65, the chemical formula should read --

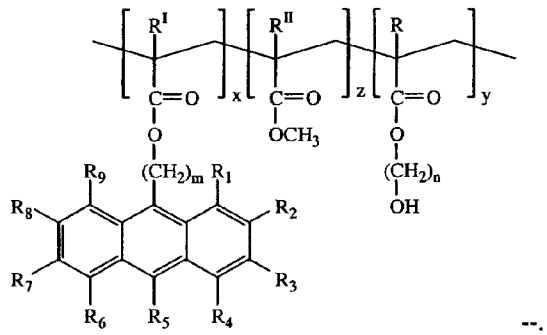

--.

Column 10,
Lines 48-59, the Chemical Formula 20 should read --

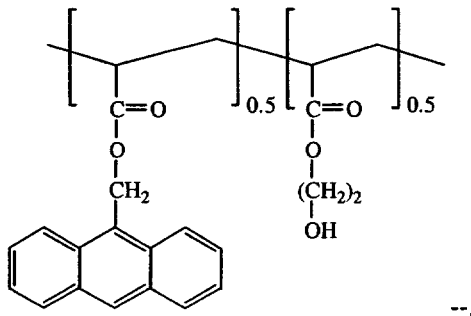

--.

UNITED STATES PATENT AND TRADEMARK OFFICE
CERTIFICATE OF CORRECTION

PATENT NO. : 6,368,768 B1
DATED : April 9, 2002
INVENTOR(S) : Min-Ho Jung, Sung-Eun Hong and Ki-Ho Baik It is certified that error appears in the above-identified patent and that said Letters Patent is hereby corrected as shown below:

Column 11,
Lines 12-25, the Chemical Formula 21 should read --

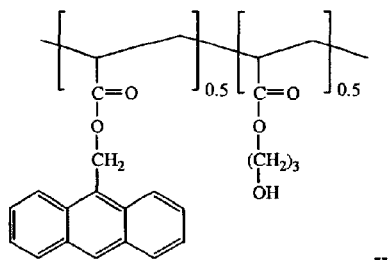

--.

Lines 45-59, the Chemical Formula 22 should read --

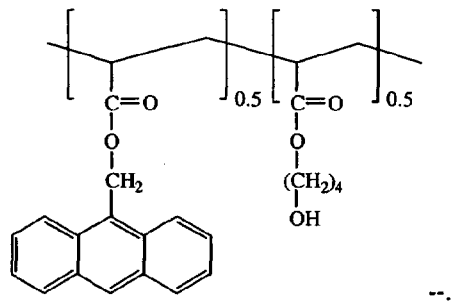

--.

Column 12,
Lines 35-50, the Chemical Formula 24 should read --

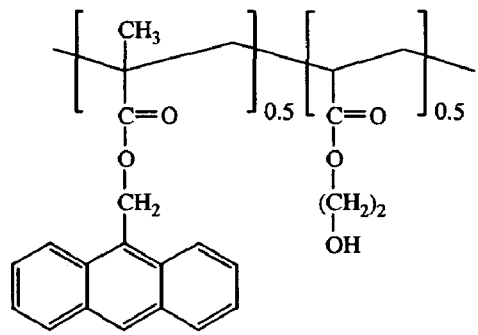

--.

UNITED STATES PATENT AND TRADEMARK OFFICE
CERTIFICATE OF CORRECTION

PATENT NO.    : 6,368,768 B1
DATED         : April 9, 2002
INVENTOR(S)   : Min-Ho Jung, Sung-Eun Hong and Ki-Ho Baik It is certified that error appears in the above-identified patent and that said Letters Patent is hereby corrected as shown below:

<u>Column 13,</u>
Lines 5-19, the Chemical Formula 25 should read --

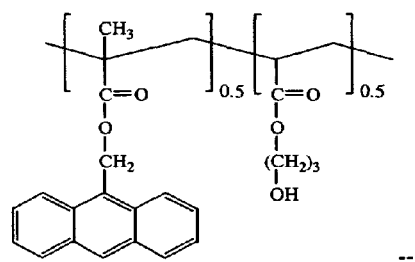

--.

Lines 40-50, the Chemical Formula 26 should read --

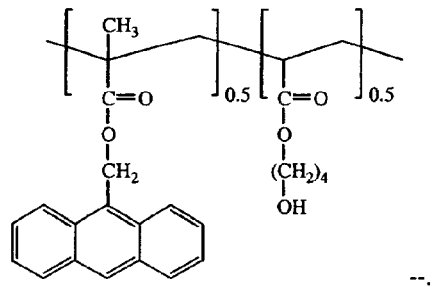

--.

<u>Column 14,</u>
Lines 10-20, the Chemical Formula 27 should read --

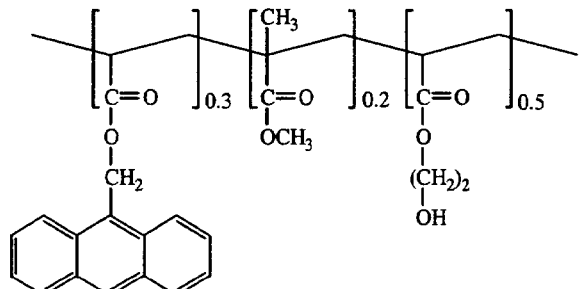

--.

UNITED STATES PATENT AND TRADEMARK OFFICE
CERTIFICATE OF CORRECTION

PATENT NO. : 6,368,768 B1
DATED : April 9, 2002
INVENTOR(S) : Min-Ho Jung, Sung-Eun Hong and Ki-Ho Baik Page 5 of 11

It is certified that error appears in the above-identified patent and that said Letters Patent is hereby corrected as shown below:

Column 14 cont'd.
Lines 39-41, should read -- filtered and dried to produce a poly[9-anthracenemethylacrylate-(3-hydroxypropylacrylate)-methylmethacrylate] copolymer, a polymer according to the --.
Lines 45-59, the Chemical Formula 28 should read --

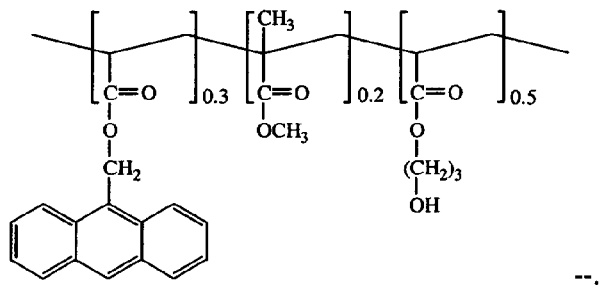

--.

Column 15,
Lines 8-9, should read -- and dried to produce a poly[9-anthracenemethylacrylate-(4-hydroxybutylacrylate)-methylmethacrylate] copolymer, a polymer --.
Lines 15-30, the Chemical Formula 29 should read --

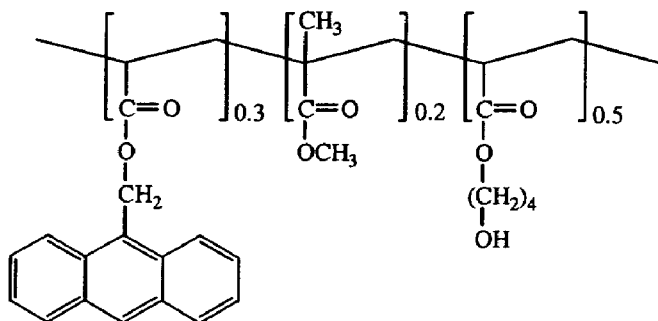

--.

Lines 46-48, should read -- the precipitate is filtered and dried to produce a poly[9-anthracenemethylmethacrylate-(2-hydroxyethylacrylate)-methylmethacrylate] copolymer, a polymer according to the --.

UNITED STATES PATENT AND TRADEMARK OFFICE
CERTIFICATE OF CORRECTION

PATENT NO. : 6,368,768 B1
DATED : April 9, 2002
INVENTOR(S) : Min-Ho Jung, Sung-Eun Hong and Ki-Ho Baik It is certified that error appears in the above-identified patent and that said Letters Patent is hereby corrected as shown below:

Column 15 cont'd.
Lines 50-65, the Chemical Formula 30 should read --

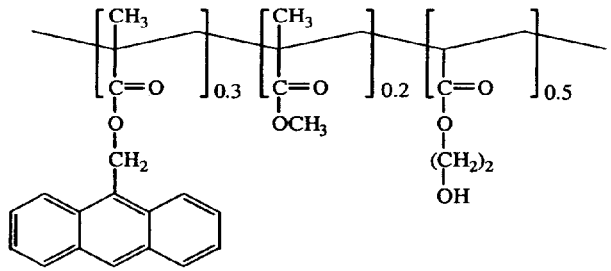

--.

Column 16,
Lines 20-22, should read -- filtered and dried to produce a poly[9-anthracenemethylmethacrylate-(3-hydroxypropylacrylate)-methylmethacrylate] copolymer, a polymer according to the --.
Lines 25-40, the Chemical Formula 31 should read --

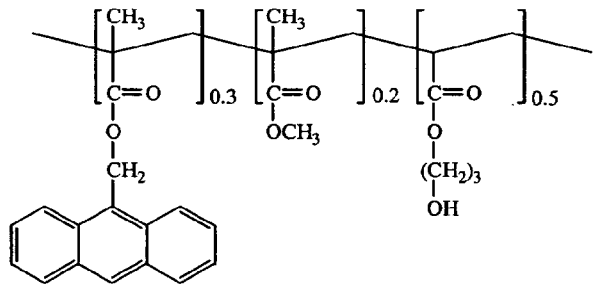

--.

Line 55, should read -- 9-anthracenemethylmethacrylate synthesized in Example IV, 0.5 --.
Lines 63-65, should read -- filtered and dried to produce a poly[9-anthracenemethylmethacrylate-(4-hydroxybutylacrylate)-methylmethacrylate] copolymer, a polymer according to the --.

Column 17,
Lines 1-15, the Chemical Formula 32 should read --

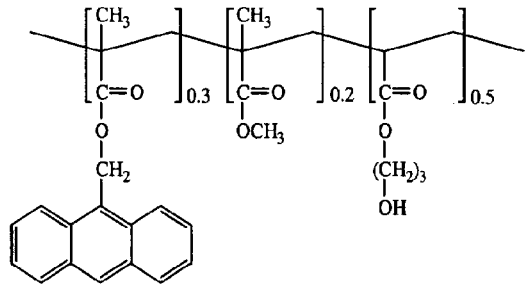

--.

UNITED STATES PATENT AND TRADEMARK OFFICE
CERTIFICATE OF CORRECTION

PATENT NO. : 6,368,768 B1
DATED : April 9, 2002
INVENTOR(S) : Min-Ho Jung, Sung-Eun Hong and Ki-Ho Baik It is certified that error appears in the above-identified patent and that said Letters Patent is hereby corrected as shown below:

Column 18,
Lines 1-15, the chemical formula 34 should read --

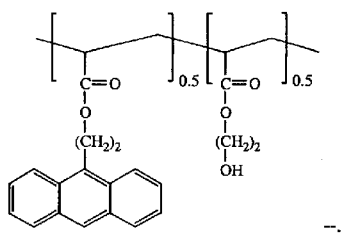

--.

Lines 40-50, the chemical formula 35 should read --

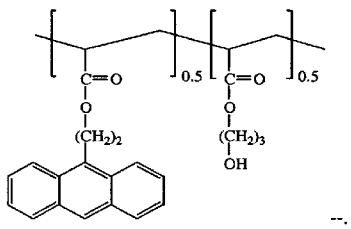

--.

Column 19,
Lines 5-20, the chemical formula 36 should read --

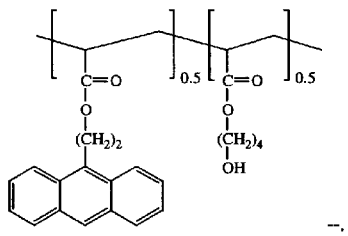

--.

Column 20,
Lines 1-15, the Chemical Formula 37 should read --

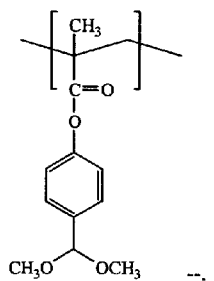

--.

UNITED STATES PATENT AND TRADEMARK OFFICE
CERTIFICATE OF CORRECTION

PATENT NO. : 6,368,768 B1
DATED : April 9, 2002
INVENTOR(S) : Min-Ho Jung, Sung-Eun Hong and Ki-Ho Baik It is certified that error appears in the above-identified patent and that said Letters Patent is hereby corrected as shown below:

Column 20 cont'd.
Lines 35-50, the Chemical Formula 38 should read --

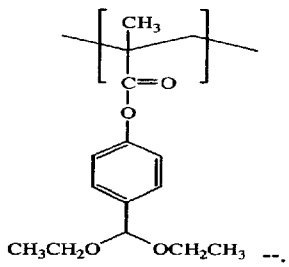

--.

Column 21,
Lines 40-60, the general formula I of Claim 1 should read --

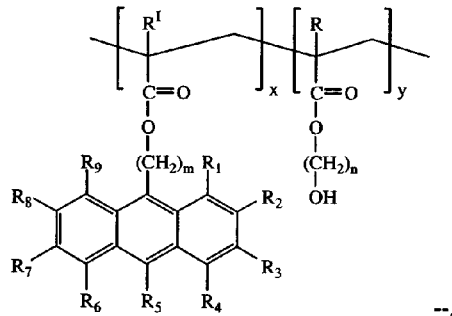

--.

Column 22,
Lines 20-35, the General Formula II in Claim 9 should read --

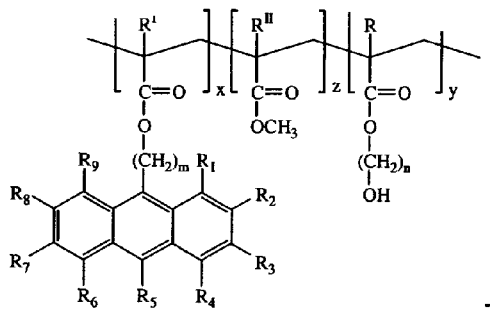

--.

UNITED STATES PATENT AND TRADEMARK OFFICE
CERTIFICATE OF CORRECTION

PATENT NO. : 6,368,768 B1
DATED : April 9, 2002
INVENTOR(S) : Min-Ho Jung, Sung-Eun Hong and Ki-Ho Baik It is certified that error appears in the above-identified patent and that said Letters Patent is hereby corrected as shown below:

Column 23,
Lines 1-20, the General Formula I in Claim 16 should read --

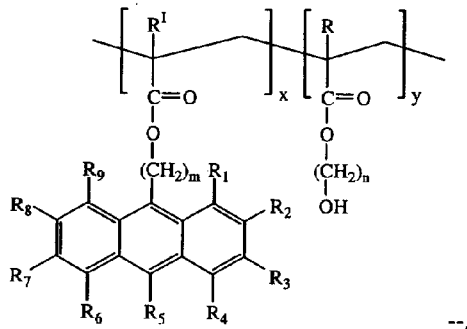

--.

Column 24,
Lines 1-20, the chemical formula III in Claim 19 should read --

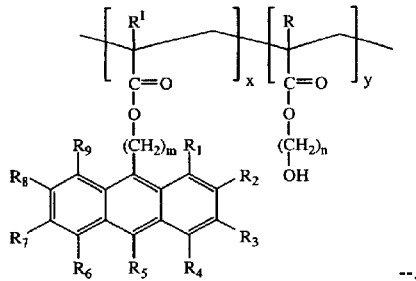

--.

Lines 50-65, the chemical formula IV in Claim 20 should read --

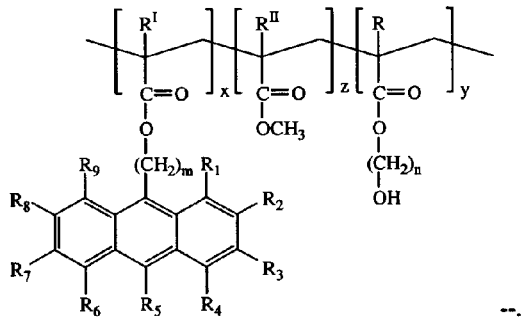

--.

UNITED STATES PATENT AND TRADEMARK OFFICE
CERTIFICATE OF CORRECTION

PATENT NO.   : 6,368,768 B1
DATED        : April 9, 2002
INVENTOR(S)  : Min-Ho Jung, Sung-Eun Hong and Ki-Ho Baik It is certified that error appears in the above-identified patent and that said Letters Patent is hereby corrected as shown below:

Column 26,
Lines 10-25, the Formula I should read --

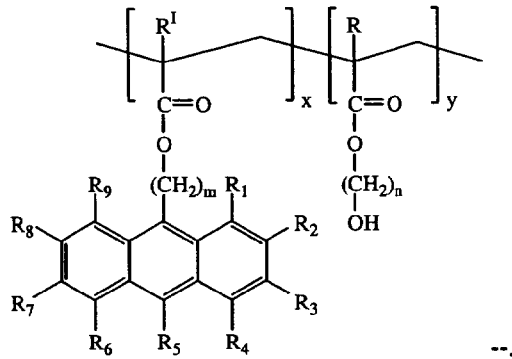

--.

Column 27,
Lines 40-55, the general formula I in Claim 32 should read --

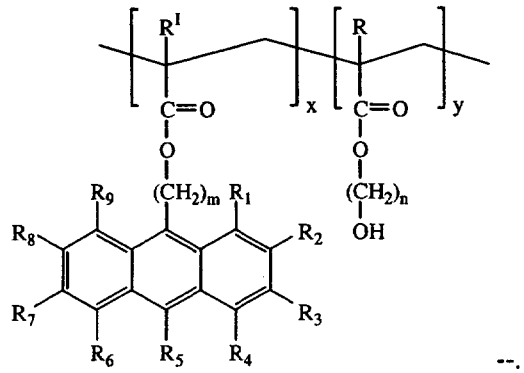

--.

UNITED STATES PATENT AND TRADEMARK OFFICE
CERTIFICATE OF CORRECTION

PATENT NO. : 6,368,768 B1
DATED : April 9, 2002
INVENTOR(S) : Min-Ho Jung, Sung-Eun Hong and Ki-Ho Baik It is certified that error appears in the above-identified patent and that said Letters Patent is hereby corrected as shown below:

Column 29,
Lines 1-20, the general formula I in Claim 35 should read --

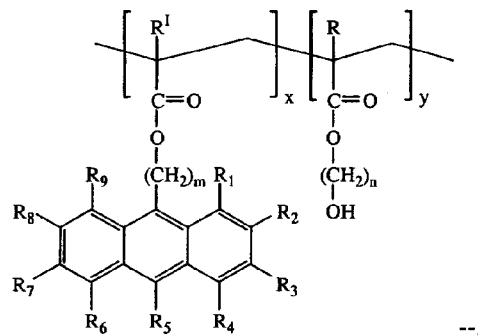

--.

Signed and Sealed this

Twenty-sixth Day of November, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,368,768 B1  Page 1 of 11
DATED : April 9, 2002
INVENTOR(S) : Min-Ho Jung, Sung-Eun Hong and Ki-Ho Baik It is certified that error appears in the above-identified patent and that said Letters Patent is hereby corrected as shown below:

Title page,
Item [57], ABSTRACT,
General Formula II should read --

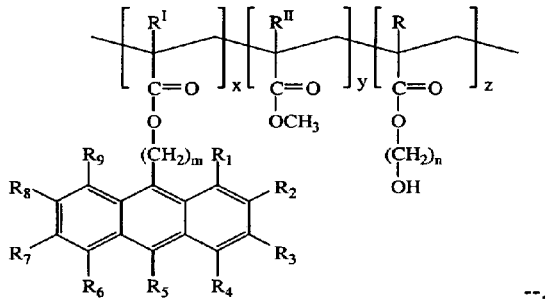

--.

Column 3,
Lines 30-45, the General Formula I should read --

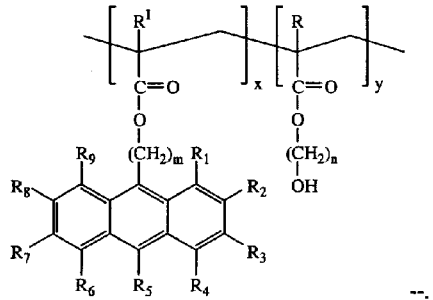

--.

Lines 50-65, the General Formula II should read --

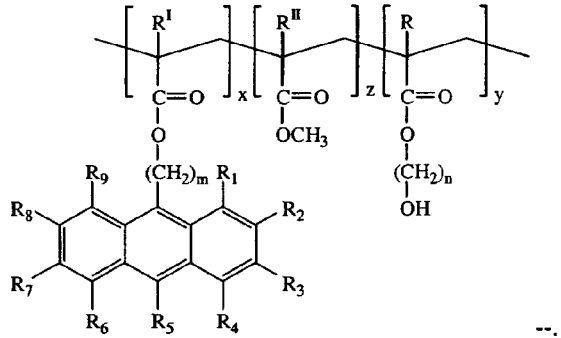

--.

UNITED STATES PATENT AND TRADEMARK OFFICE
CERTIFICATE OF CORRECTION

PATENT NO. : 6,368,768 B1
DATED : April 9, 2002
INVENTOR(S) : Min-Ho Jung, Sung-Eun Hong and Ki-Ho Baik It is certified that error appears in the above-identified patent and that said Letters Patent is hereby corrected as shown below:

Column 5,
Lines 1-19, the chemical formula should read --

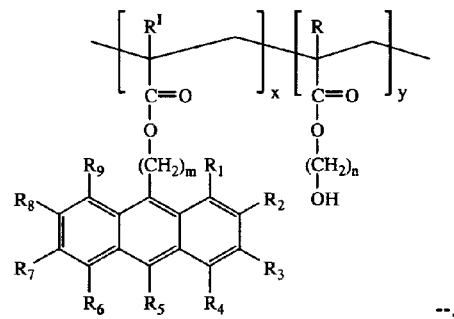

--.

Lines 50-65, the chemical formula should read --

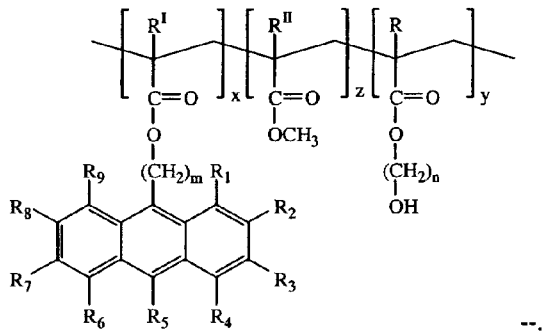

--.

Column 10,
Lines 48-59, the Chemical Formula 20 should read --

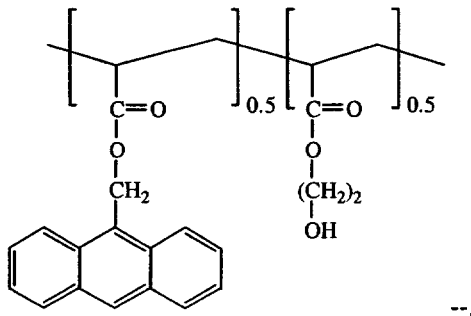

--.

UNITED STATES PATENT AND TRADEMARK OFFICE
CERTIFICATE OF CORRECTION

PATENT NO. : 6,368,768 B1
DATED : April 9, 2002
INVENTOR(S) : Min-Ho Jung, Sung-Eun Hong and Ki-Ho Baik It is certified that error appears in the above-identified patent and that said Letters Patent is hereby corrected as shown below:

Column 11,
Lines 12-25, the Chemical Formula 21 should read --

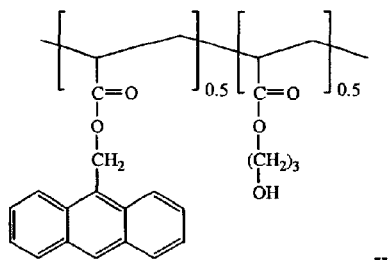

--.

Lines 45-59, the Chemical Formula 22 should read --

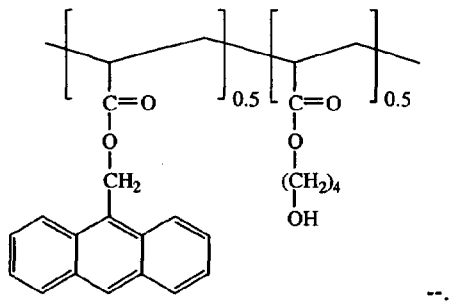

--.

Column 12,
Lines 35-50, the Chemical Formula 24 should read --

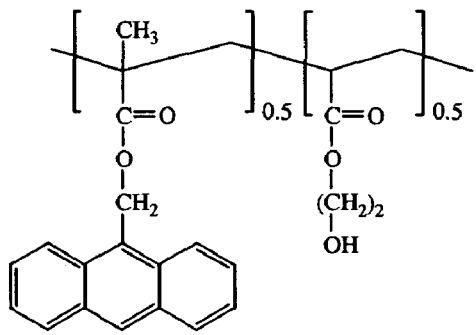

--.

UNITED STATES PATENT AND TRADEMARK OFFICE
CERTIFICATE OF CORRECTION

PATENT NO. : 6,368,768 B1
DATED : April 9, 2002
INVENTOR(S) : Min-Ho Jung, Sung-Eun Hong and Ki-Ho Baik It is certified that error appears in the above-identified patent and that said Letters Patent is hereby corrected as shown below:

Column 13,
Lines 5-19, the Chemical Formula 25 should read --

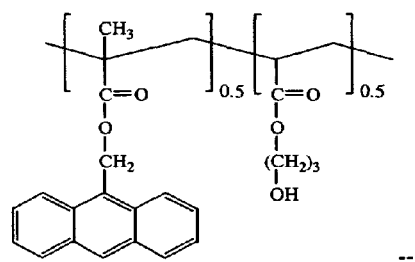

--.

Lines 40-50, the Chemical Formula 26 should read --

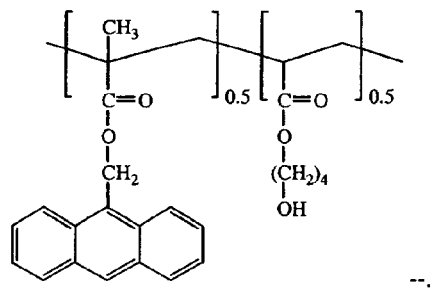

--.

Column 14,
Lines 10-20, the Chemical Formula 27 should read --

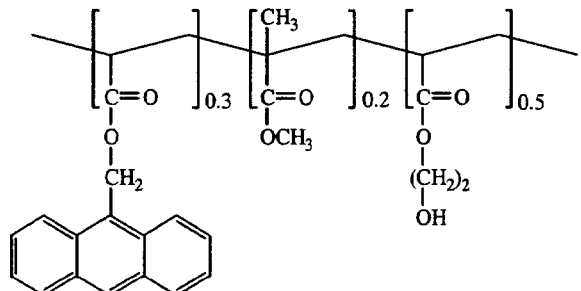

--.

UNITED STATES PATENT AND TRADEMARK OFFICE
CERTIFICATE OF CORRECTION

PATENT NO. : 6,368,768 B1
DATED : April 9, 2002
INVENTOR(S) : Min-Ho Jung, Sung-Eun Hong and Ki-Ho Baik It is certified that error appears in the above-identified patent and that said Letters Patent is hereby corrected as shown below:

Column 14 cont'd.
Lines 39-41, should read -- filtered and dried to produce a poly[9-anthracenemethylacrylate-(3-hydroxypropylacrylate)-methylmethacrylate] copolymer, a polymer according to the --.
Lines 45-59, the Chemical Formula 28 should read --

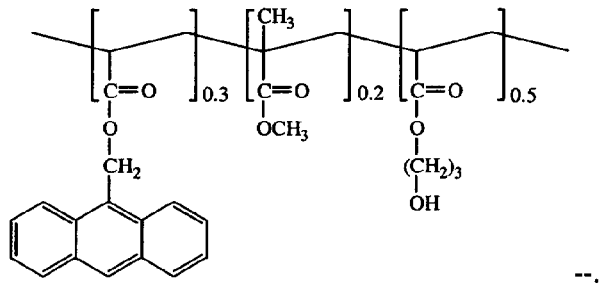

--.

Column 15,
Lines 8-9, should read -- and dried to produce a poly[9-anthracenemethylacrylate-(4-hydroxybutylacrylate)-methylmethacrylate] copolymer, a polymer --.
Lines 15-30, the Chemical Formula 29 should read --

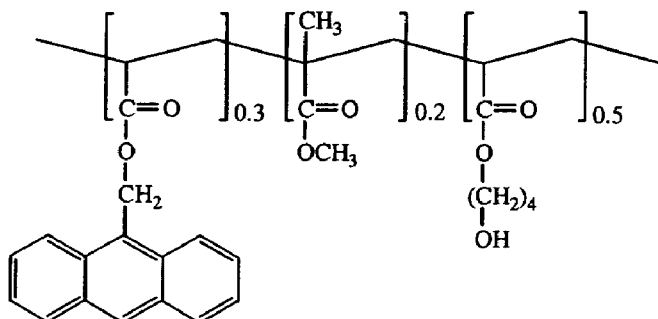

--.

Lines 46-48, should read -- the precipitate is filtered and dried to produce a poly[9-anthracenemethylmethacrylate-(2-hydroxyethylacrylate)-methylmethacrylate] copolymer, a polymer according to the --.

UNITED STATES PATENT AND TRADEMARK OFFICE
CERTIFICATE OF CORRECTION

PATENT NO.    : 6,368,768 B1
DATED         : April 9, 2002
INVENTOR(S)   : Min-Ho Jung, Sung-Eun Hong and Ki-Ho Baik It is certified that error appears in the above-identified patent and that said Letters Patent is hereby corrected as shown below:

Column 15 cont'd.
Lines 50-65, the Chemical Formula 30 should read --

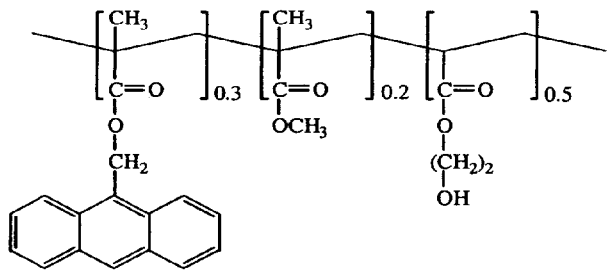

--.

Column 16,
Lines 20-22, should read -- filtered and dried to produce a poly[9-anthracenemethylmethacrylate-(3-hydroxypropylacrylate)-methylmethacrylate] copolymer, a polymer according to the --.
Lines 25-40, the Chemical Formula 31 should read --

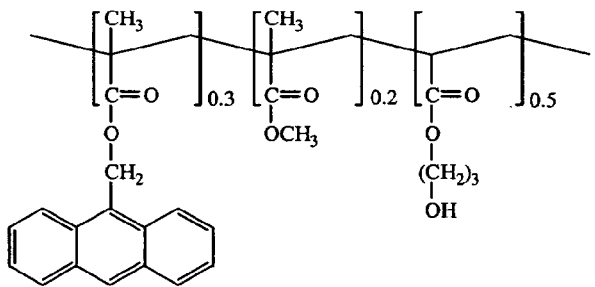

--.

Line 55, should read -- 9-anthracenemethylmethacrylate synthesized in Example IV, 0.5 --.
Lines 63-65, should read -- filtered and dried to produce a poly[9-anthracenemethylmethacrylate-(4-hydroxybutylacrylate)-methylmethacrylate] copolymer, a polymer according to the --.

Column 17,
Lines 1-15, the Chemical Formula 32 should read --

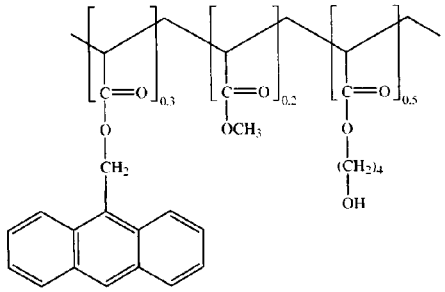

UNITED STATES PATENT AND TRADEMARK OFFICE
CERTIFICATE OF CORRECTION

PATENT NO. : 6,368,768 B1
DATED : April 9, 2002
INVENTOR(S) : Min-Ho Jung, Sung-Eun Hong and Ki-Ho Baik It is certified that error appears in the above-identified patent and that said Letters Patent is hereby corrected as shown below:

Column 18,
Lines 1-15, the chemical formula 34 should read --

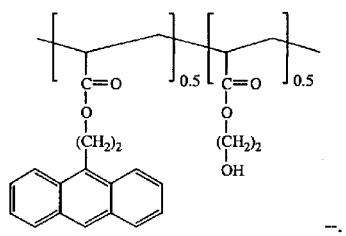

--.

Lines 40-50, the chemical formula 35 should read --

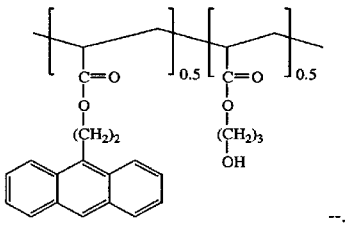

--.

Column 19,
Lines 5-20, the chemical formula 36 should read --

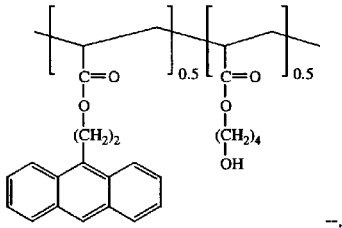

--.

Column 20,
Lines 1-15, the Chemical Formula 37 should read --

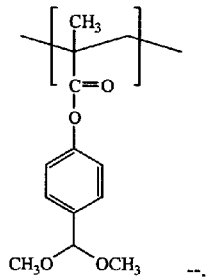

--.

UNITED STATES PATENT AND TRADEMARK OFFICE
CERTIFICATE OF CORRECTION

PATENT NO.    : 6,368,768 B1
DATED         : April 9, 2002
INVENTOR(S)   : Min-Ho Jung, Sung-Eun Hong and Ki-Ho Baik It is certified that error appears in the above-identified patent and that said Letters Patent is hereby corrected as shown below:

Column 20 cont'd.
Lines 35-50, the Chemical Formula 38 should read --

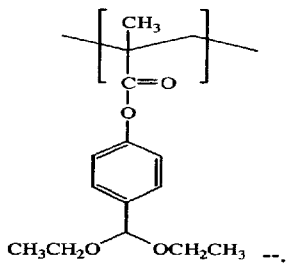

Column 21,
Lines 40-60, the general formula I of Claim 1 should read --

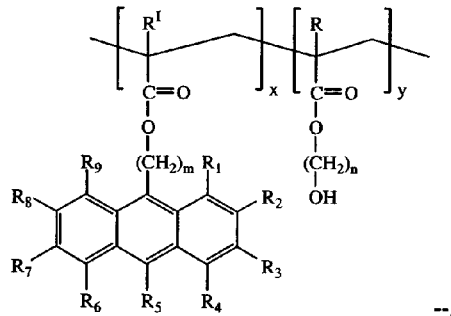

--.

Column 22,
Lines 20-35, the General Formula II in Claim 9 should read --

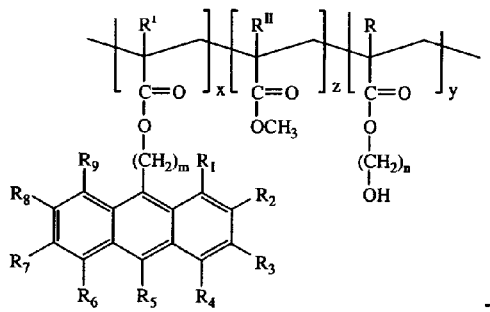

--.

UNITED STATES PATENT AND TRADEMARK OFFICE
CERTIFICATE OF CORRECTION

PATENT NO. : 6,368,768 B1
DATED : April 9, 2002
INVENTOR(S) : Min-Ho Jung, Sung-Eun Hong and Ki-Ho Baik It is certified that error appears in the above-identified patent and that said Letters Patent is hereby corrected as shown below:

Column 23,
Lines 1-20, the General Formula I in Claim 16 should read --

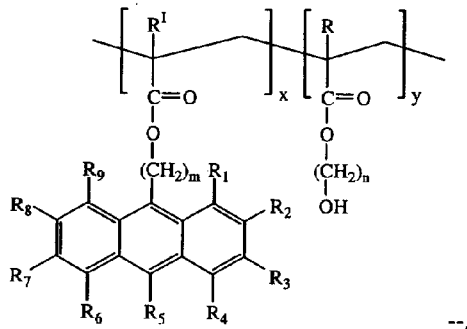

--.

Column 24,
Lines 1-20, the chemical formula III in Claim 19 should read --

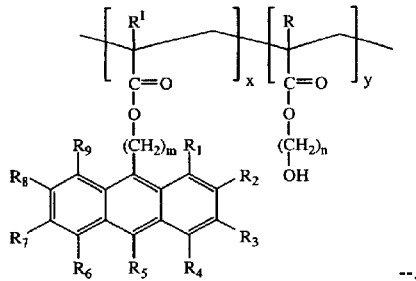

--.

Lines 50-65, the chemical formula IV in Claim 20 should read --

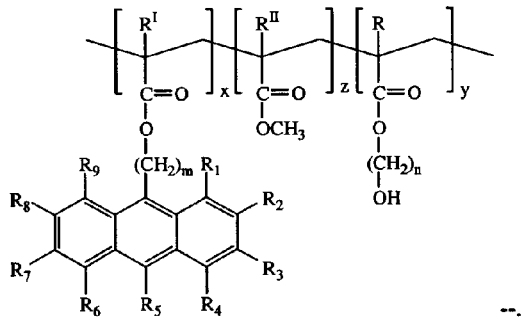

--.

UNITED STATES PATENT AND TRADEMARK OFFICE
CERTIFICATE OF CORRECTION

PATENT NO. : 6,368,768 B1
DATED : April 9, 2002
INVENTOR(S) : Min-Ho Jung, Sung-Eun Hong and Ki-Ho Baik It is certified that error appears in the above-identified patent and that said Letters Patent is hereby corrected as shown below:

Column 26,
Lines 10-25, the Formula I should read --

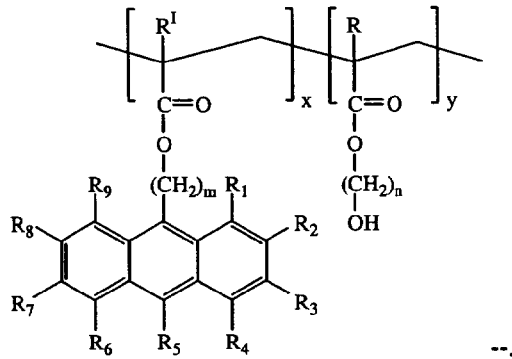

--.

Column 27,
Lines 40-55, the general formula I in Claim 32 should read --

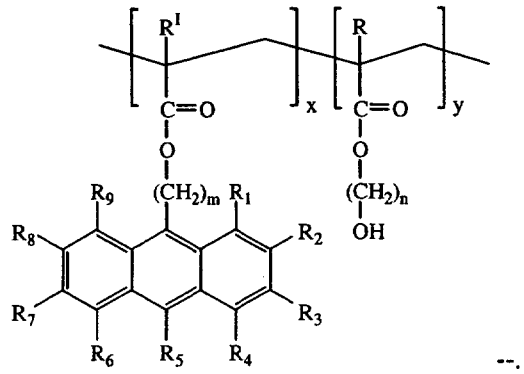

--.

UNITED STATES PATENT AND TRADEMARK OFFICE
CERTIFICATE OF CORRECTION

PATENT NO.    : 6,368,768 B1
DATED         : April 9, 2002
INVENTOR(S)   : Min-Ho Jung, Sung-Eun Hong and Ki-Ho Baik It is certified that error appears in the above-identified patent and that said Letters Patent is hereby corrected as shown below:

Column 29,
Lines 1-20, the general formula I in Claim 35 should read --

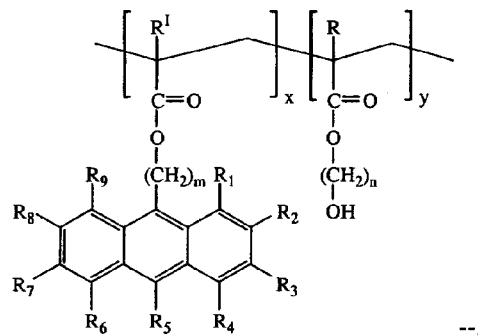

--.

This certificate supersedes Certificate of Correction issued November 26, 2002.

Signed and Sealed this

Seventeenth Day of June, 2003

JAMES E. ROGAN
*Director of the United States Patent and Trademark Office*